US012636316B2

(12) United States Patent
Han et al.

(10) Patent No.: US 12,636,316 B2
(45) Date of Patent: May 26, 2026

(54) PHARMACEUTICAL COMPOSITION FOR PREVENTING OR TREATING MYOSITIS, COMPRISING ISOLATED MITOCHONDRIA AS ACTIVE INGREDIENT

(71) Applicant: PAEAN BIOTECHNOLOGY INC., Daejeon (KR)

(72) Inventors: Kyuboem Han, Daejeon (KR); Chun-Hyung Kim, Sejong (KR); Shin-Hye Yu, Daejeon (KR); Seo-Eun Lee, Daejeon (KR); Sang-Min Lim, Incheon (KR); Hahnsun Jung, Gunpo-si (KR); Kwangmin Na, Gwangmyeong-si (KR); Yoon Mi Han, Seoul (KR); Jun Young Son, Seoul (KR); Eun Young Lee, Seoul (KR); Jeong Yeon Kim, Seoul (KR); Yeong Wook Song, Seoul (KR); Jin Chul Paeng, Seoul (KR); Yun Sang Lee, Yongin-si (KR); Do Won Hwang, Yeongtong (KR)

(73) Assignee: Paean Biotechnology Inc., Daejeon (KR)

( * ) Notice: Subject to any disclaimer, the term of this patent is extended or adjusted under 35 U.S.C. 154(b) by 731 days.

(21) Appl. No.: 17/607,850

(22) PCT Filed: Apr. 29, 2020

(86) PCT No.: PCT/KR2020/005769
§ 371 (c)(1),
(2) Date: Oct. 29, 2021

(87) PCT Pub. No.: WO2020/222566
PCT Pub. Date: Nov. 5, 2020

(65) Prior Publication Data
US 2022/0211754 A1 Jul. 7, 2022

(30) Foreign Application Priority Data
Apr. 30, 2019 (KR) ........................ 10-2019-0050527

(51) Int. Cl.
| | |
|---|---|
| A61K 35/12 | (2015.01) |
| A61K 35/17 | (2015.01) |
| A61K 35/19 | (2015.01) |
| A61K 35/28 | (2015.01) |
| A61K 35/30 | (2015.01) |
| A61K 35/33 | (2015.01) |
| A61K 35/34 | (2015.01) |
| A61K 35/35 | (2015.01) |
| A61K 35/50 | (2015.01) |
| A61K 35/52 | (2015.01) |
| A61K 35/54 | (2015.01) |
| A61K 35/545 | (2015.01) |

(52) U.S. Cl.
CPC .............. *A61K 35/12* (2013.01); *A61K 35/17* (2013.01); *A61K 35/19* (2013.01); *A61K 35/28* (2013.01); *A61K 35/30* (2013.01); *A61K 35/33* (2013.01); *A61K 35/34* (2013.01); *A61K 35/35* (2013.01); *A61K 35/50* (2013.01); *A61K 35/52* (2013.01); *A61K 35/54* (2013.01); *A61K 35/545* (2013.01)

(58) Field of Classification Search
None
See application file for complete search history.

(56) References Cited

U.S. PATENT DOCUMENTS

| | | |
|---|---|---|
| 2019/0111016 A1 | 4/2019 | Cortopassi et al. |
| 2020/0009198 A1 | 1/2020 | Choi et al. |

FOREIGN PATENT DOCUMENTS

| | | | |
|---|---|---|---|
| JP | 2016518357 A | | 6/2016 |
| KR | 10-2018-0062387 A | | 6/2018 |
| KR | 20180062387 | * | 6/2018 |
| RU | 2680801 C2 | | 2/2019 |
| TW | 200815381 A | | 4/2008 |
| WO | WO 2008/137035 A1 | | 11/2008 |
| WO | WO 2014117999 A1 | | 8/2014 |
| WO | WO 2014168973 A2 | | 10/2014 |
| WO | WO 2017152044 A1 | | 9/2017 |
| WO | WO 2018101708 A1 | | 6/2018 |

OTHER PUBLICATIONS

Molnar et al. Acta Neuropathol. 1998, 96, pp. 41-51.*
Meyer et al. Acta Neuropathol, 2017, 134, pp. 655-666.*
Mashkovsky, Medicines, 14th edition, vol. 1, 2002. (3 pages) in the co-pending counterpart Russian Application No. 2021134793/04(073480). The reference is characterized on p. 4 of the English translation of the Russian Office Action submitted herewith.
Office Action, dated Jul. 21, 2023, for Russian Patent Application No. 2021134793/04(073480). (16 pages) (with English Translation).

(Continued)

*Primary Examiner* — Vera Afremova
(74) *Attorney, Agent, or Firm* — Seed IP Law Group LLP

(57) ABSTRACT
The present invention relates to a pharmaceutical composition for preventing or treating myositis. More particularly, the present invention relates to a pharmaceutical composition for preventing or treating myositis, comprising mitochondria as an active ingredient. When the pharmaceutical composition of the present invention comprising exogenous mitochondria as an active ingredient is administered to a subject suffering from myositis, inflammatory cells infiltrated into the muscle cells of the subject can be reduced. In addition, the pharmaceutical composition of the present invention effectively inhibits the expression of IL-1β, TNF-α, and IL-6, inflammatory cytokines. Therefore, the pharmaceutical composition according to the present invention can be usefully used for preventing or treating myositis.

6 Claims, 29 Drawing Sheets
Specification includes a Sequence Listing.

(56)                  References Cited

OTHER PUBLICATIONS

Office Action, dated Jun. 29, 2023, for Taiwanese Patent Application No. 109114410. (9 pages) (with English Translation).

Extended European Search Report, mailed Jun. 3, 2022, for European Patent Application No. 20798096.2. (8 pages).

Kim et al., "Therapeutic effect of anti-C-X-C motif chemokine 10 (CXCL10) antibody on C protein-induced myositis mouse," *Arthritis Research & Therapy* 16(R126):1-10, 2014.

Oldfors et al., "Mitochondrial abnormalities in inclusion-body myositis," *Neurology* 66(Supp 1):S49-S55, Jan. 2006.

Rygiel et al., "Mitochondrial and inflammatory changes in sporadic inclusion body myositis," *Neuropathology and Applied Neurobiology* 41:288-303, 2015.

Sugihara et al., "A New Murine Model to Define the Critical Pathologic and Therapeutic Mediators of Polymyositis," *Arthritis & Rheumatism* 56(4):1304-1314, Apr. 2007.

Suomalainen et al., "Mitochondrial diseases: the contribution of organelle stress responses to pathology," *Nat Rev Mol Cell Biol.* Feb. 2018;19(2):77-92. Epub Aug. 9, 2017.

Mantegazza et al., "Inflammatory Myopathies: Dermatomyositis, Polymyositis and Inclusion Body Myositis," Madame Curie Bioscience Database, retrived from URL=https://www.ncbi.nih.gov/books/NBK6196/?report=printable, on Feb. 19, 2026. (19 pages).

Zeng et al., "Antibody Therapies in Autoimmune Inflammatory Myopathies: Promising Treatment Options," Neurotherapeutics 19:911-930, Apr. 8, 2022. (11 pages).

\* cited by examiner

【FIG.1】
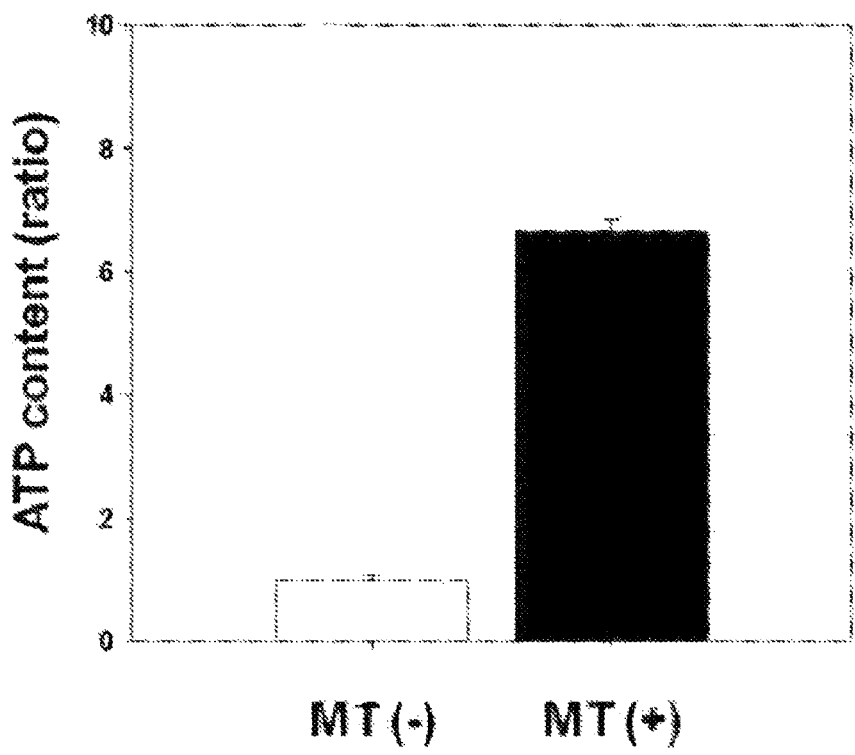
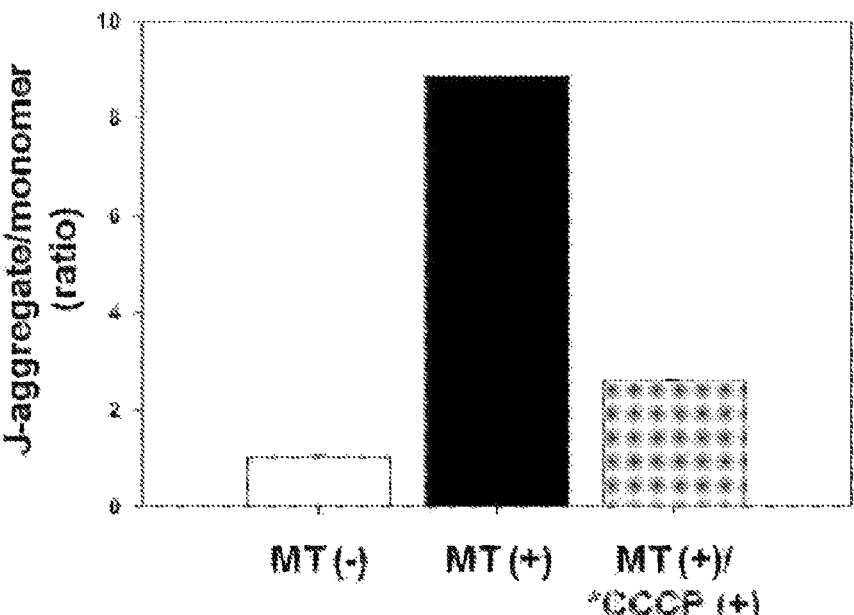
【FIG.2】

【FIG.3】
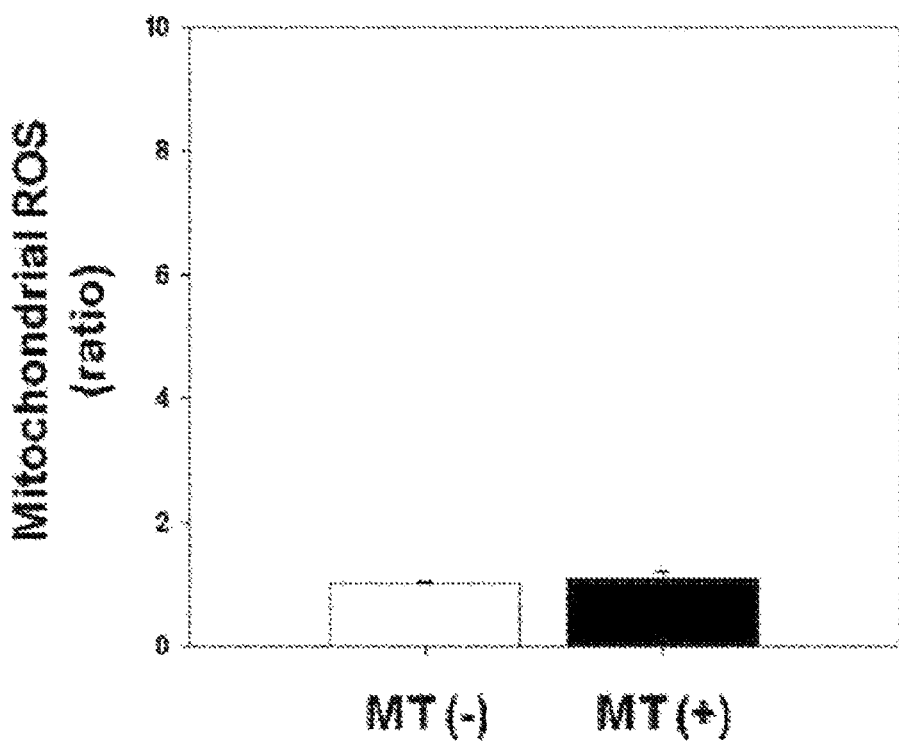

[FIG.4]
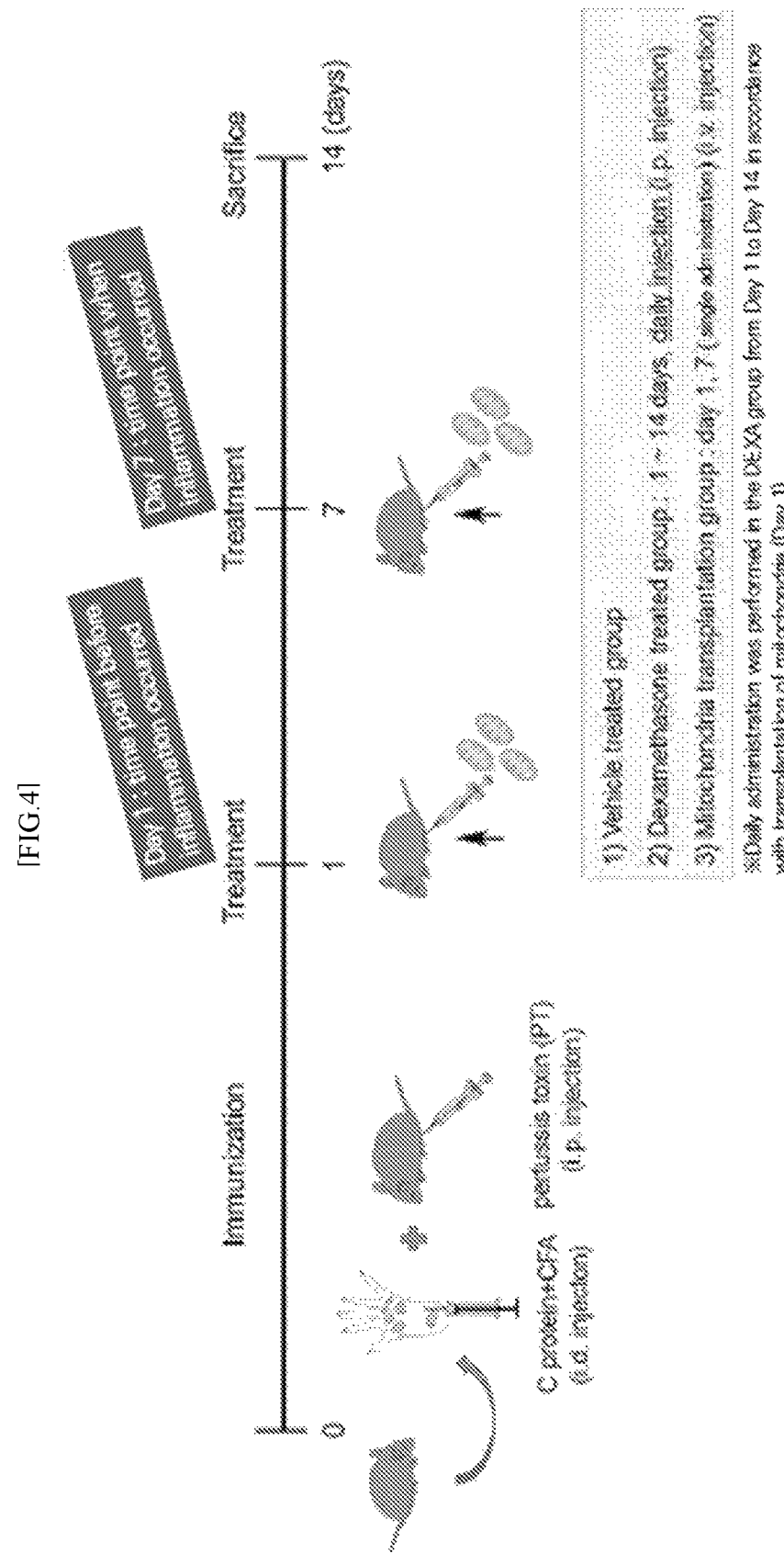

[FIG.5]
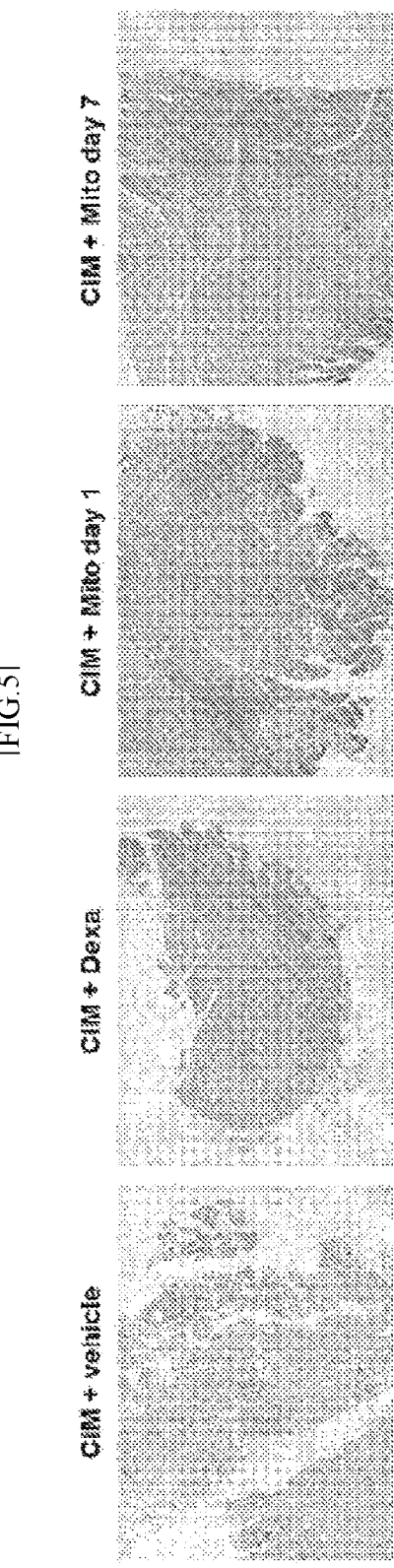

【FIG.6】
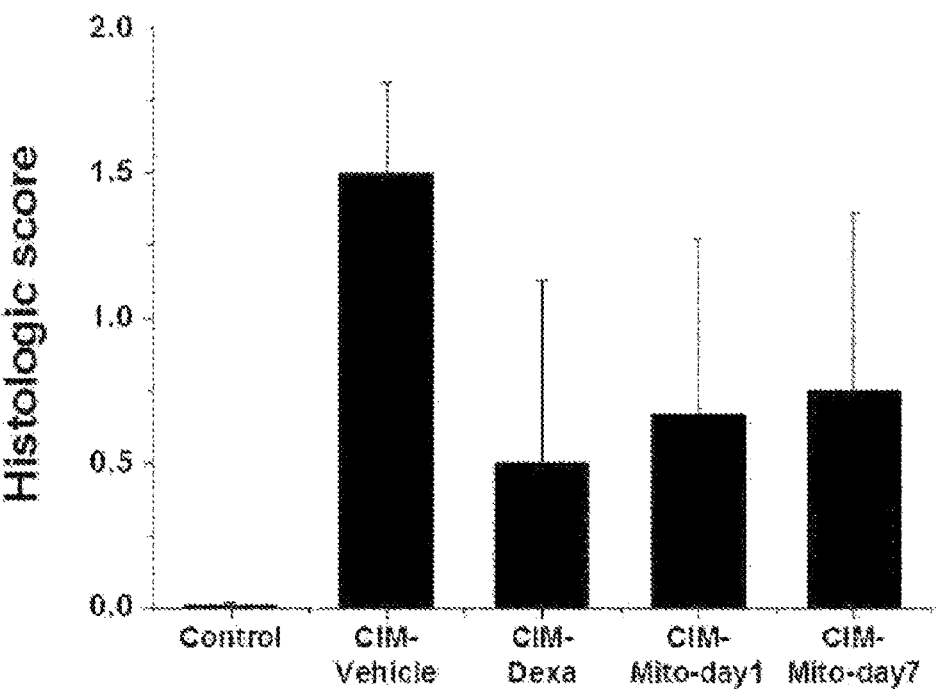
【FIG.7】
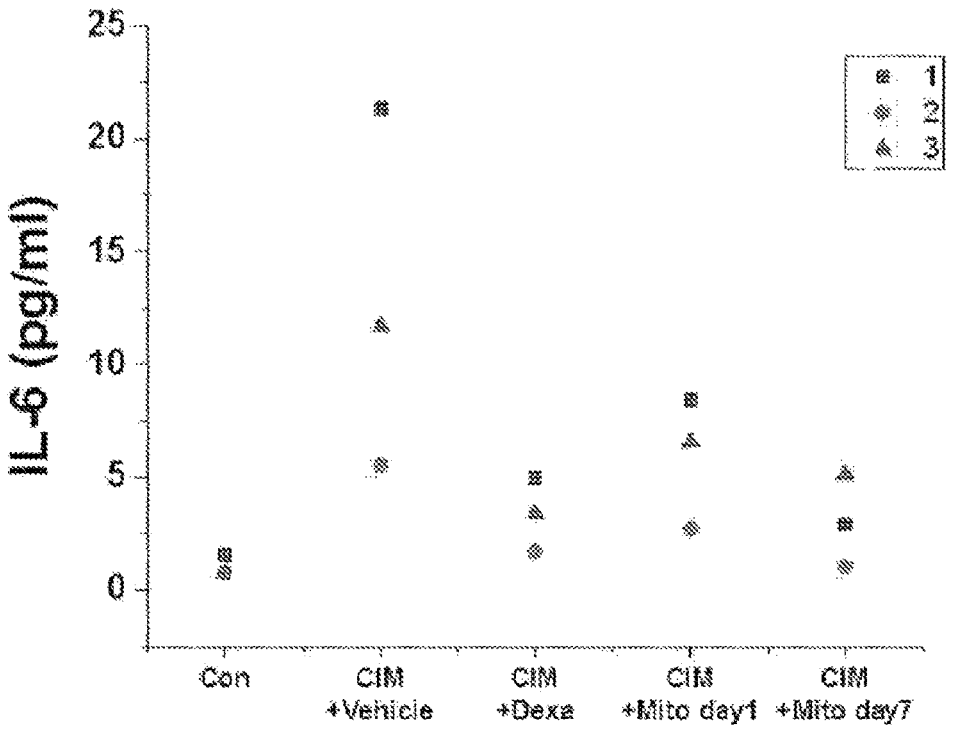

【FIG.8】
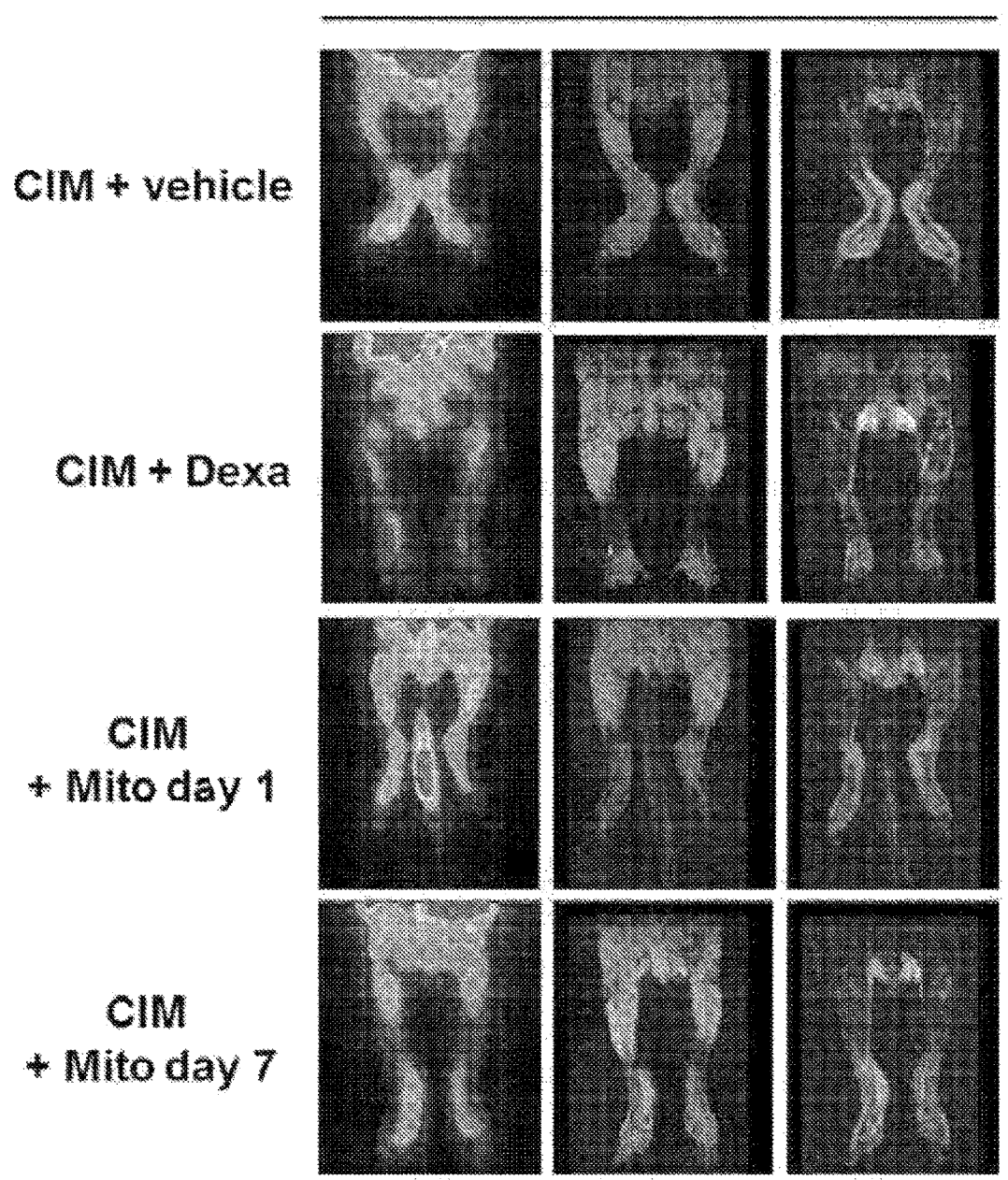

[FIG.9]
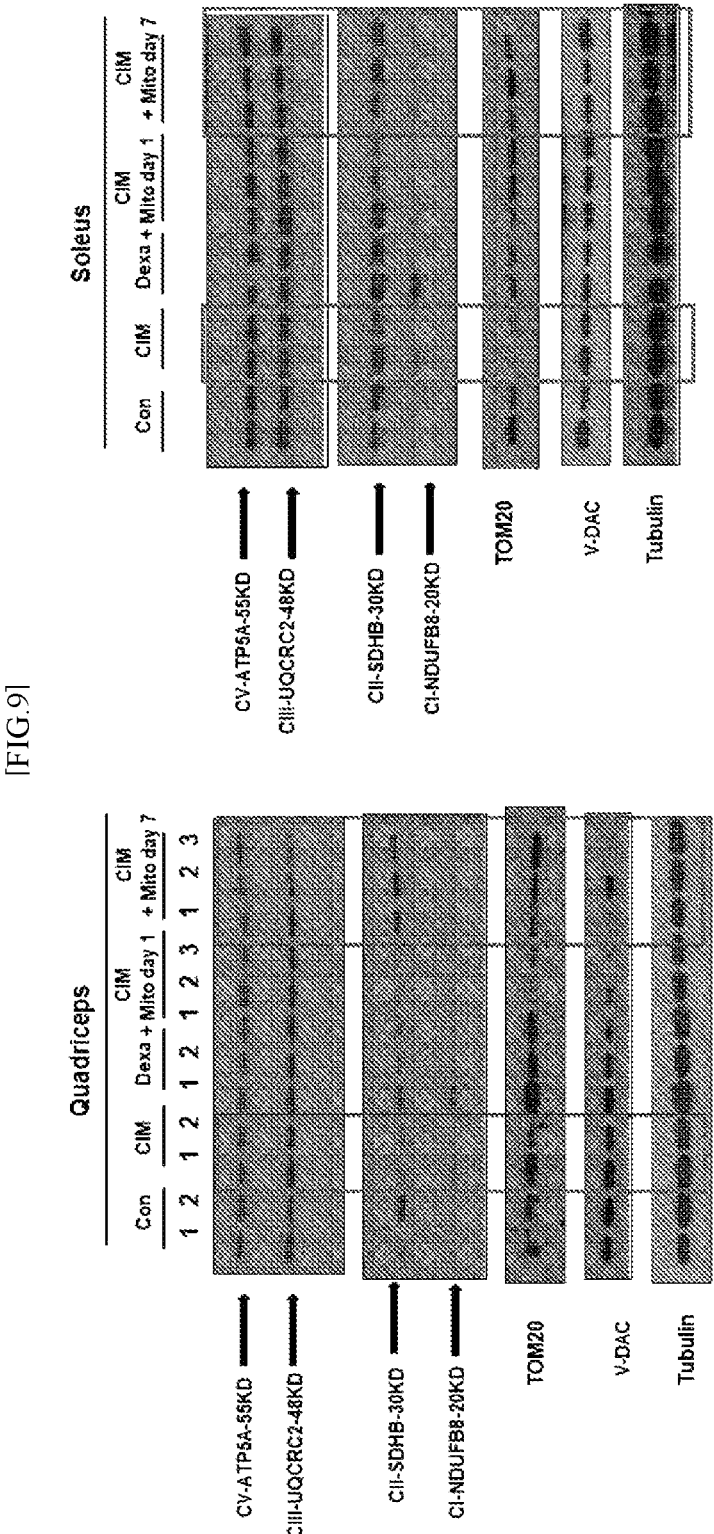

[FIG.10]
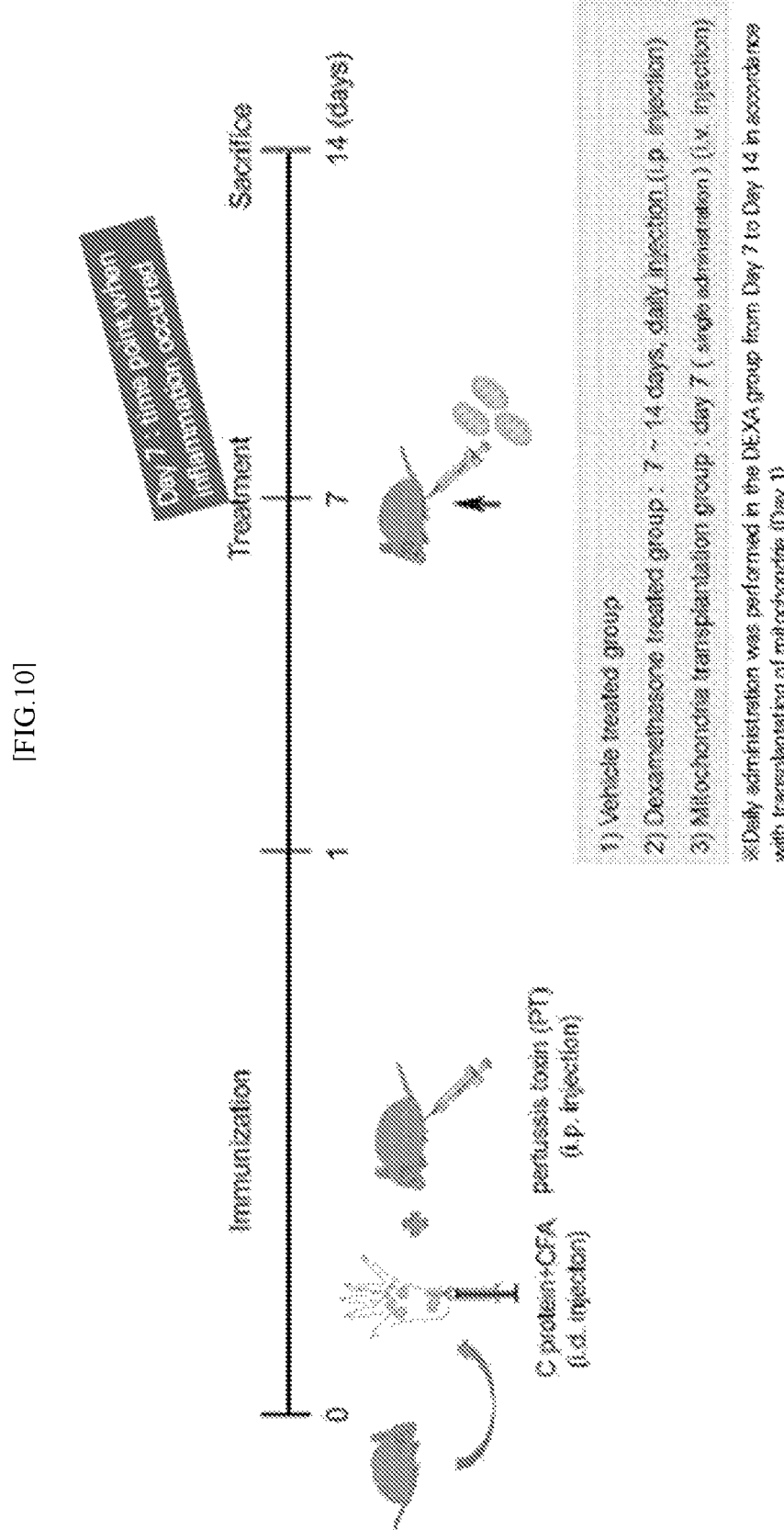

[FIG.11]
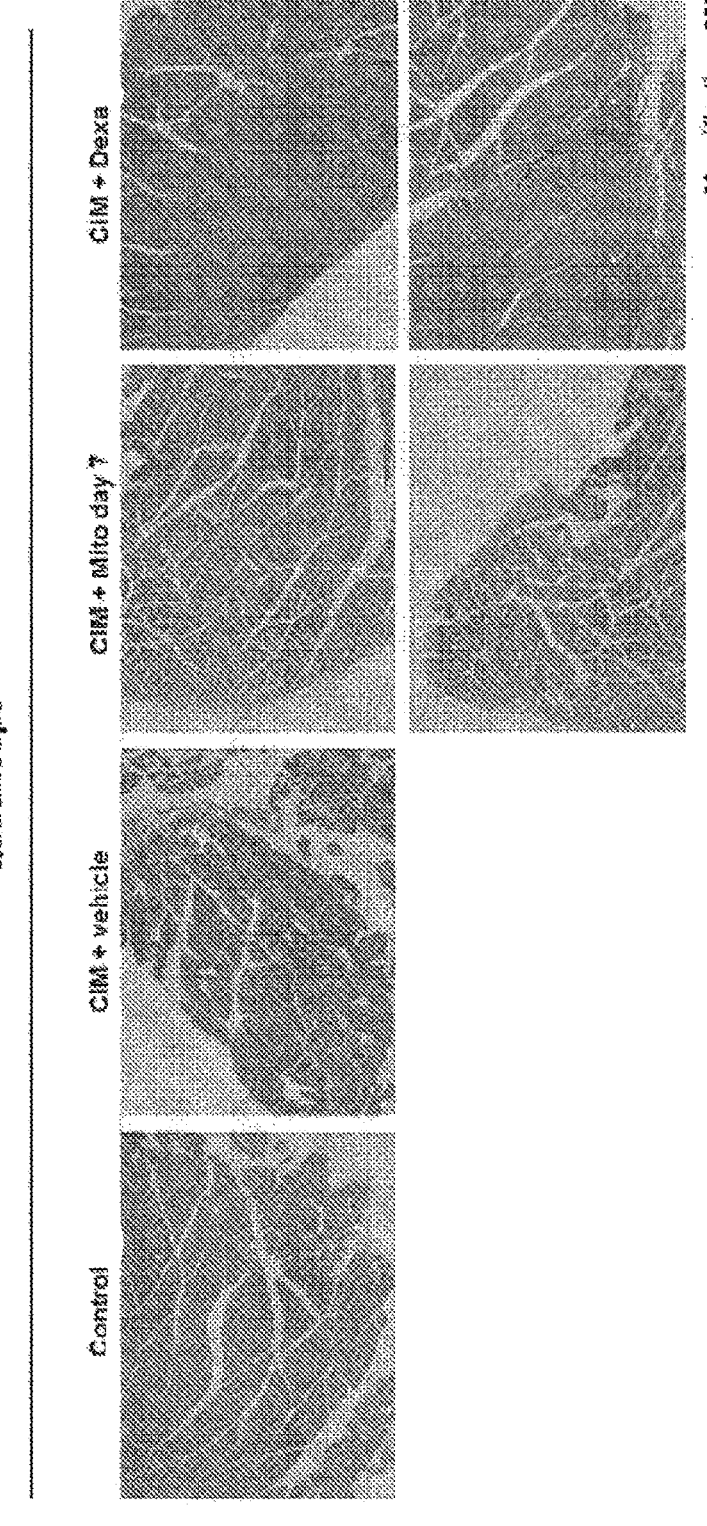

[FIG.12]

Hamstring

Control    CIM + vehicle    CIM + Mito day 7    CIM + Dexa

Magnification x200

【FIG.13】
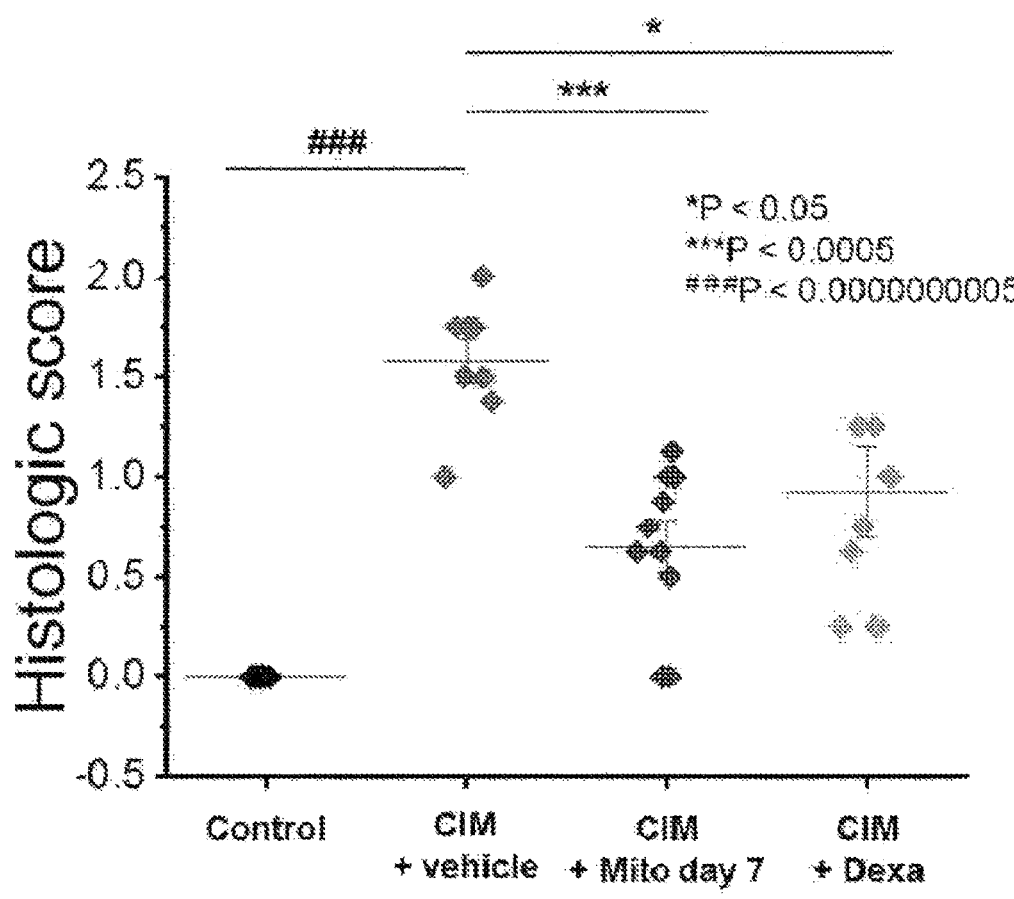

【FIG.14】
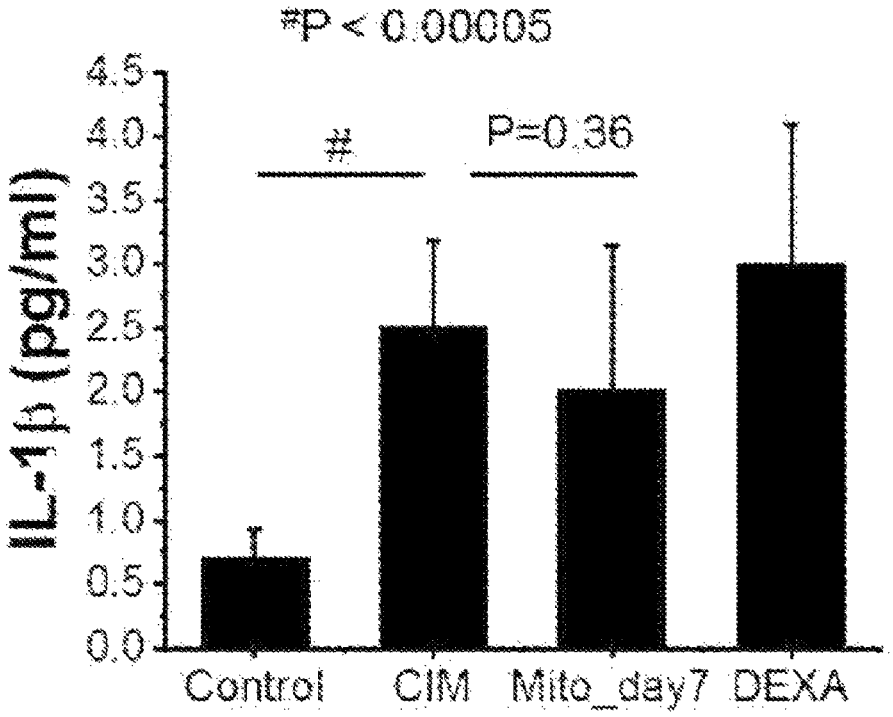
【FIG.15】
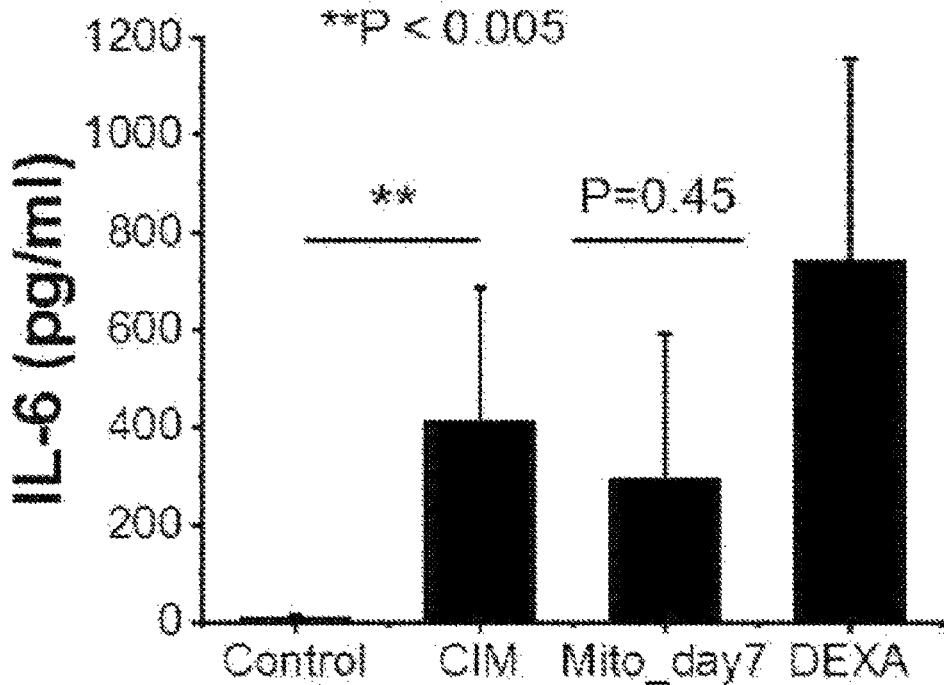

【FIG.16】
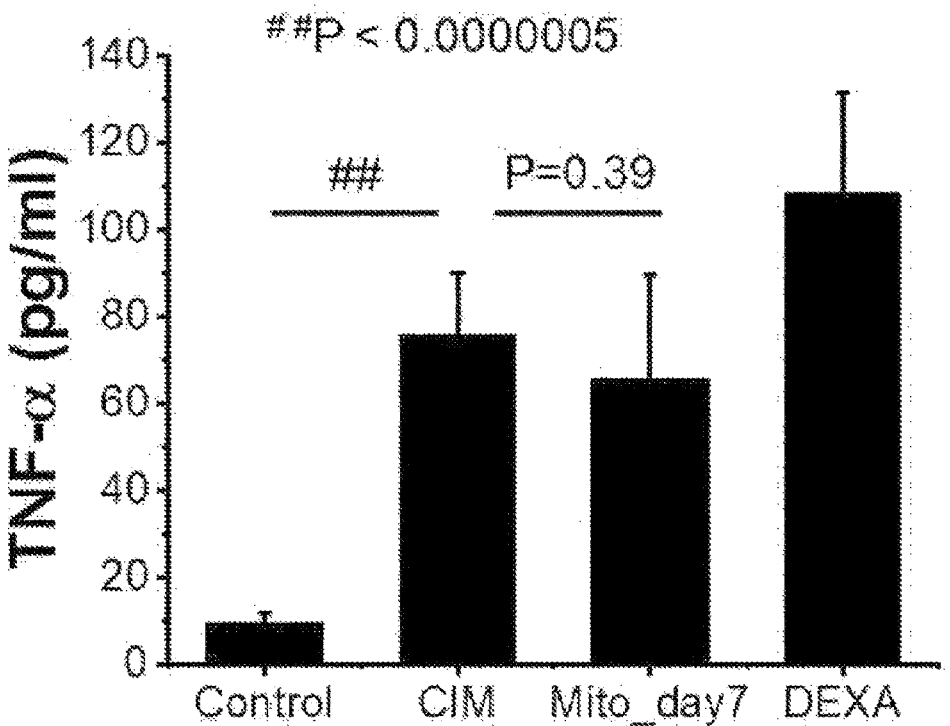
【FIG.17】
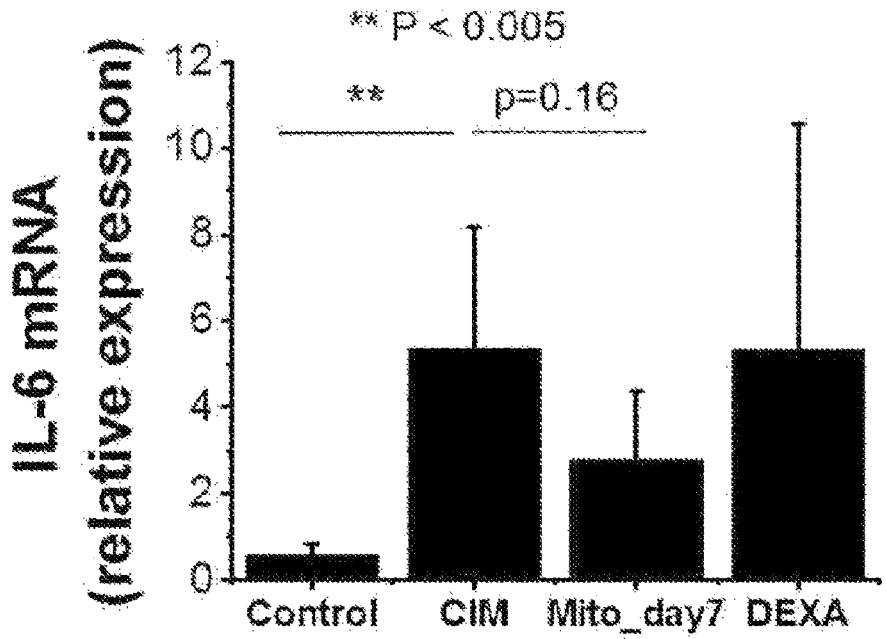

[FIG.18]
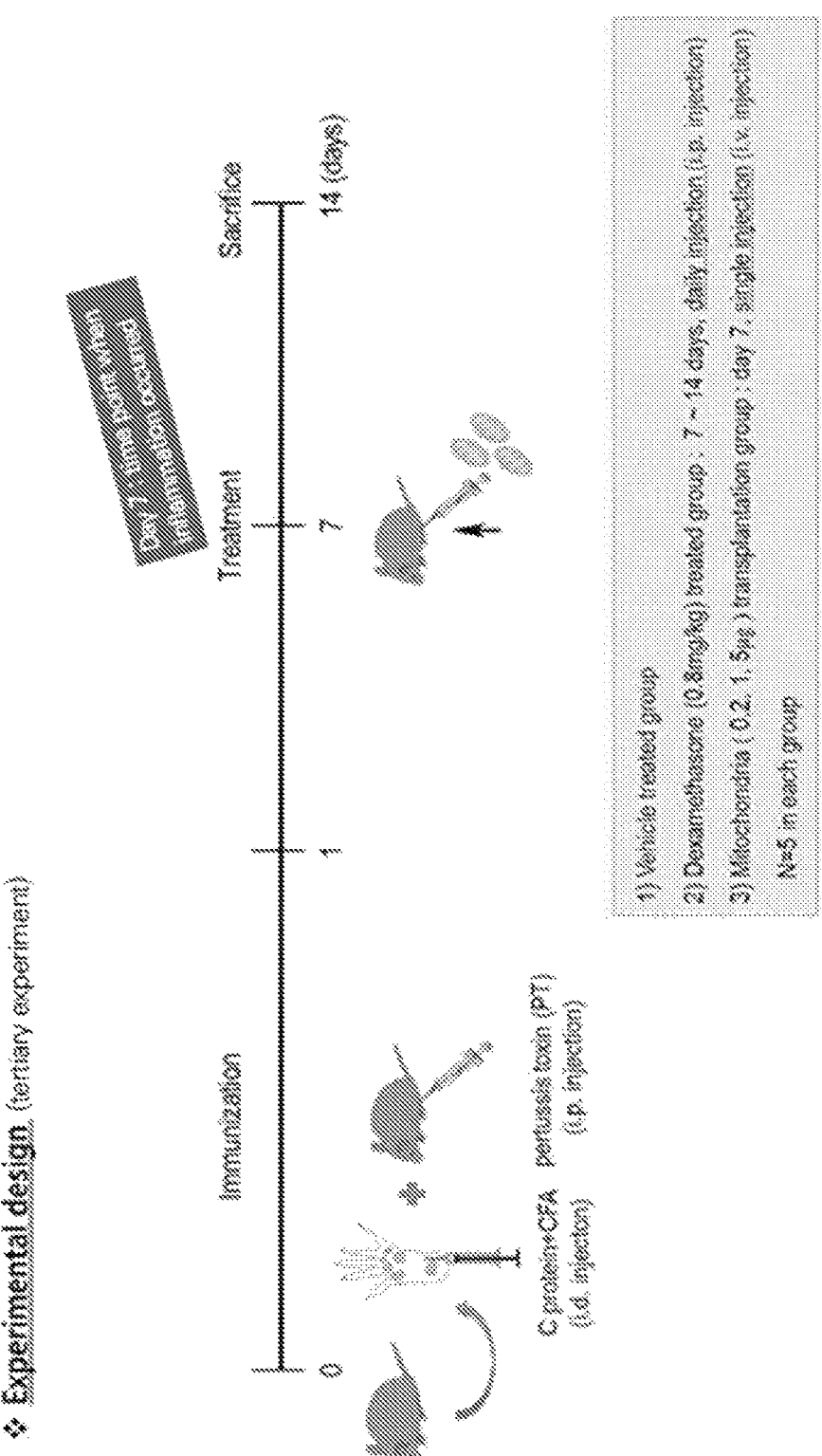

[FIG.19]
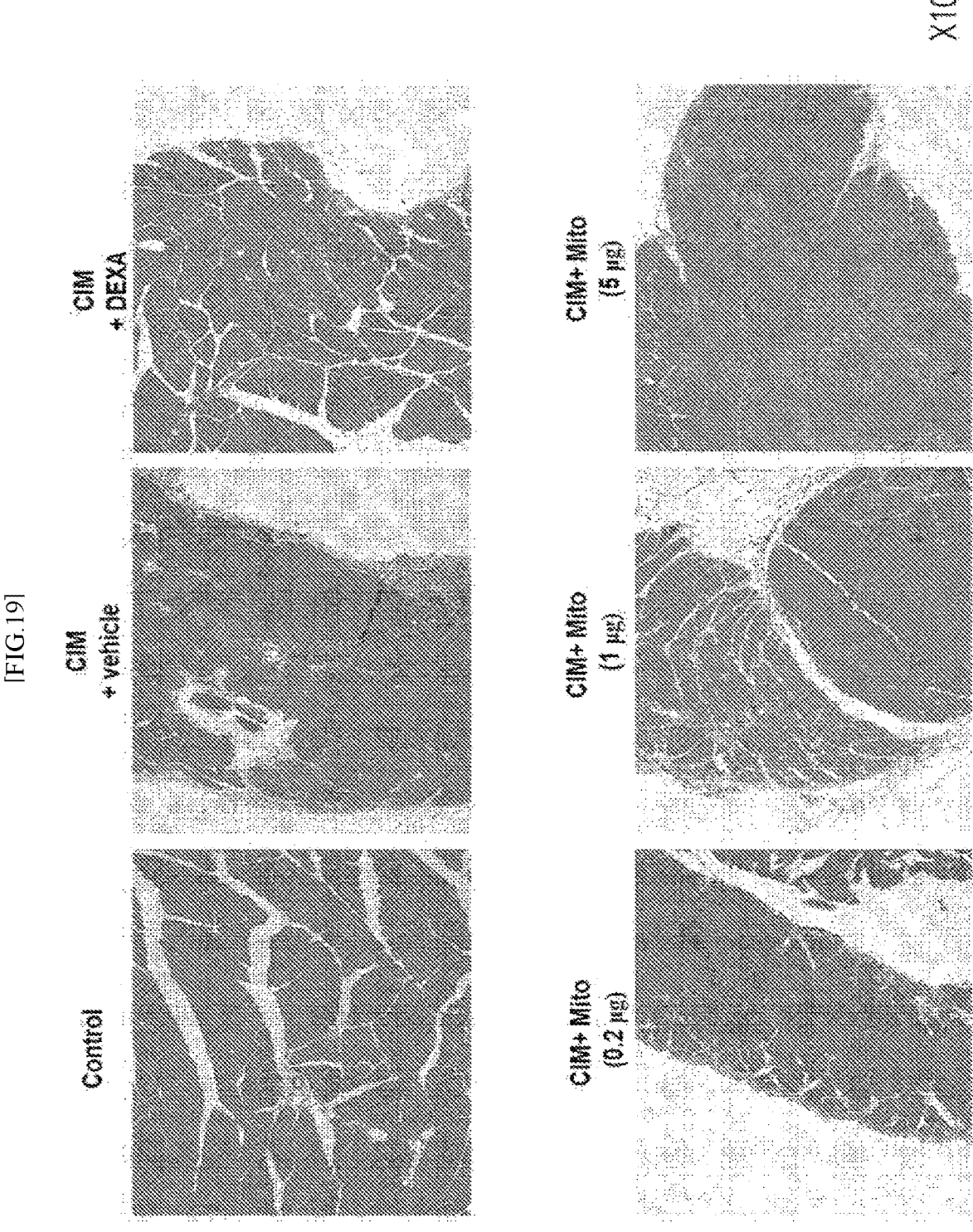

【FIG.20】
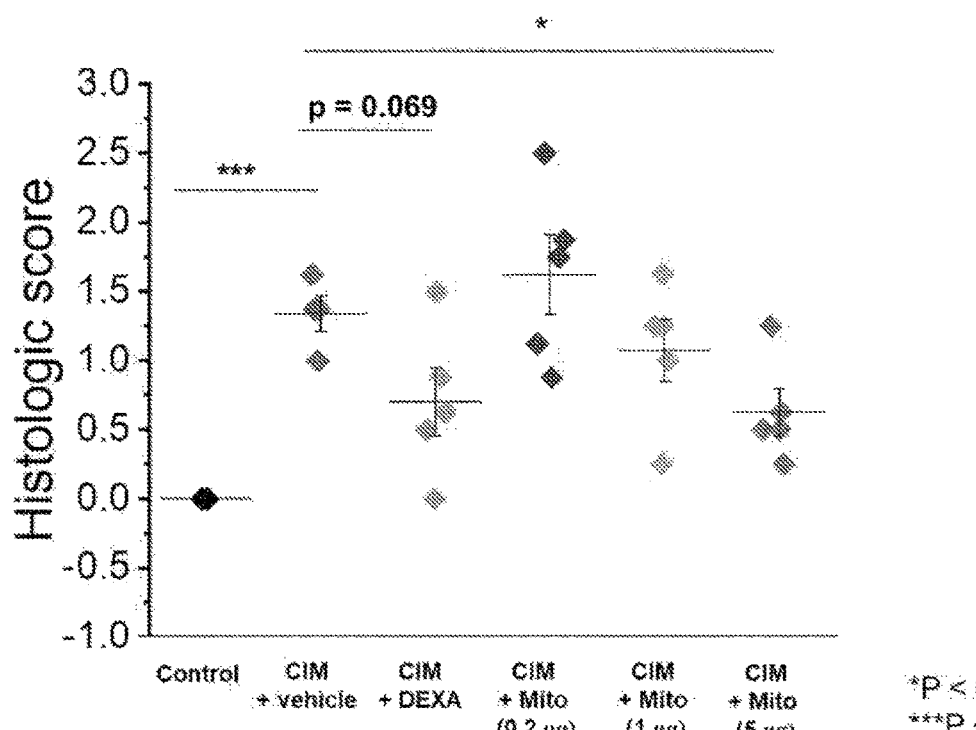

[FIG.21]
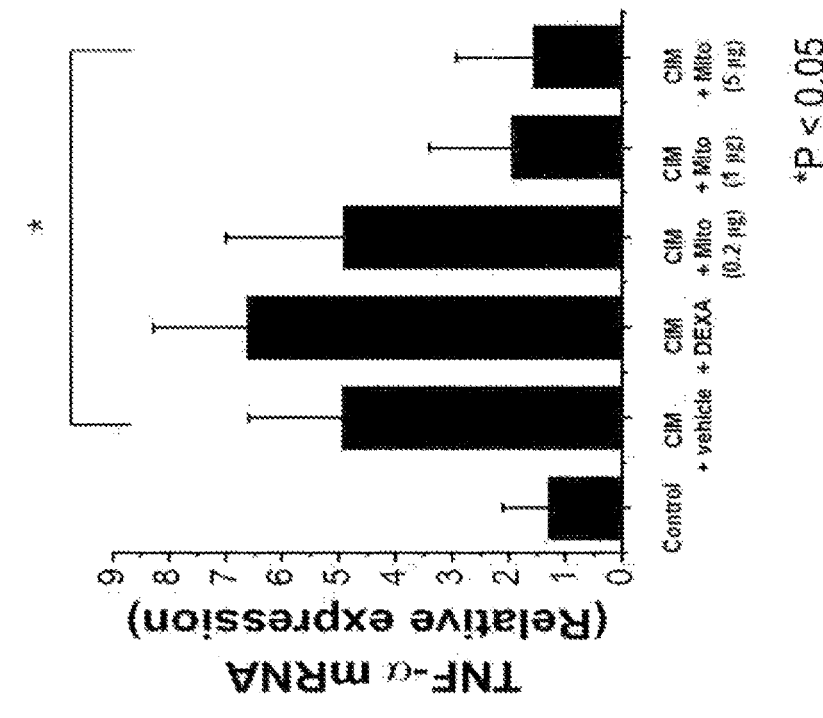

【FIG.22】
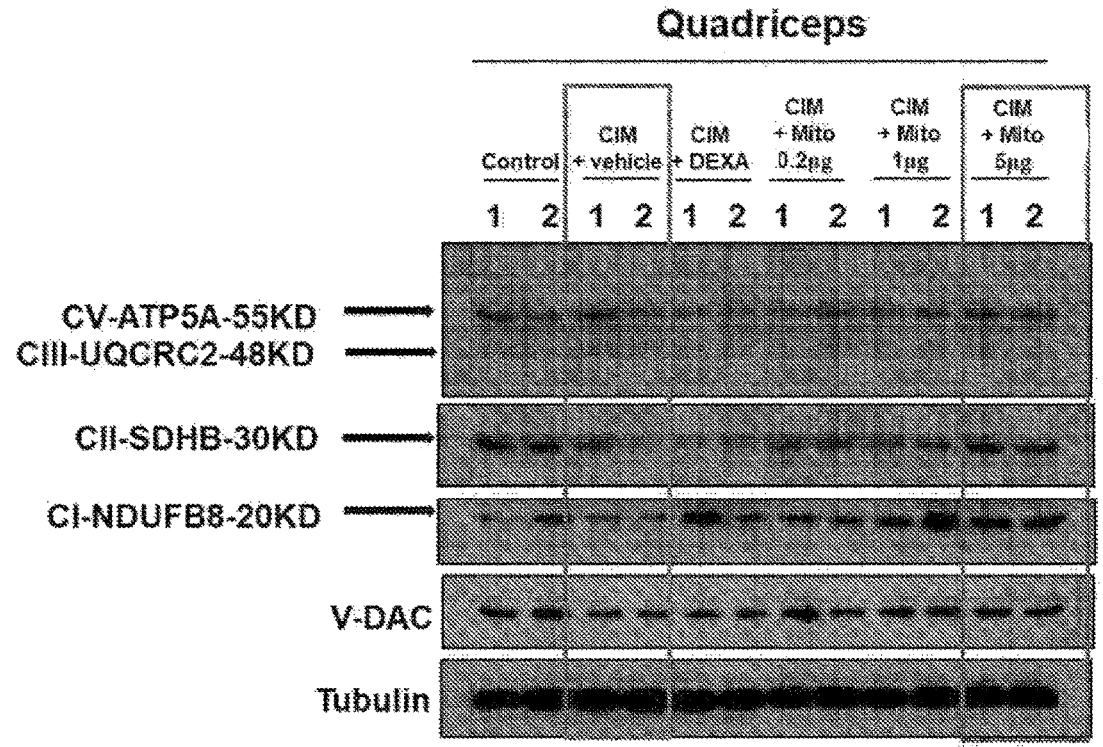

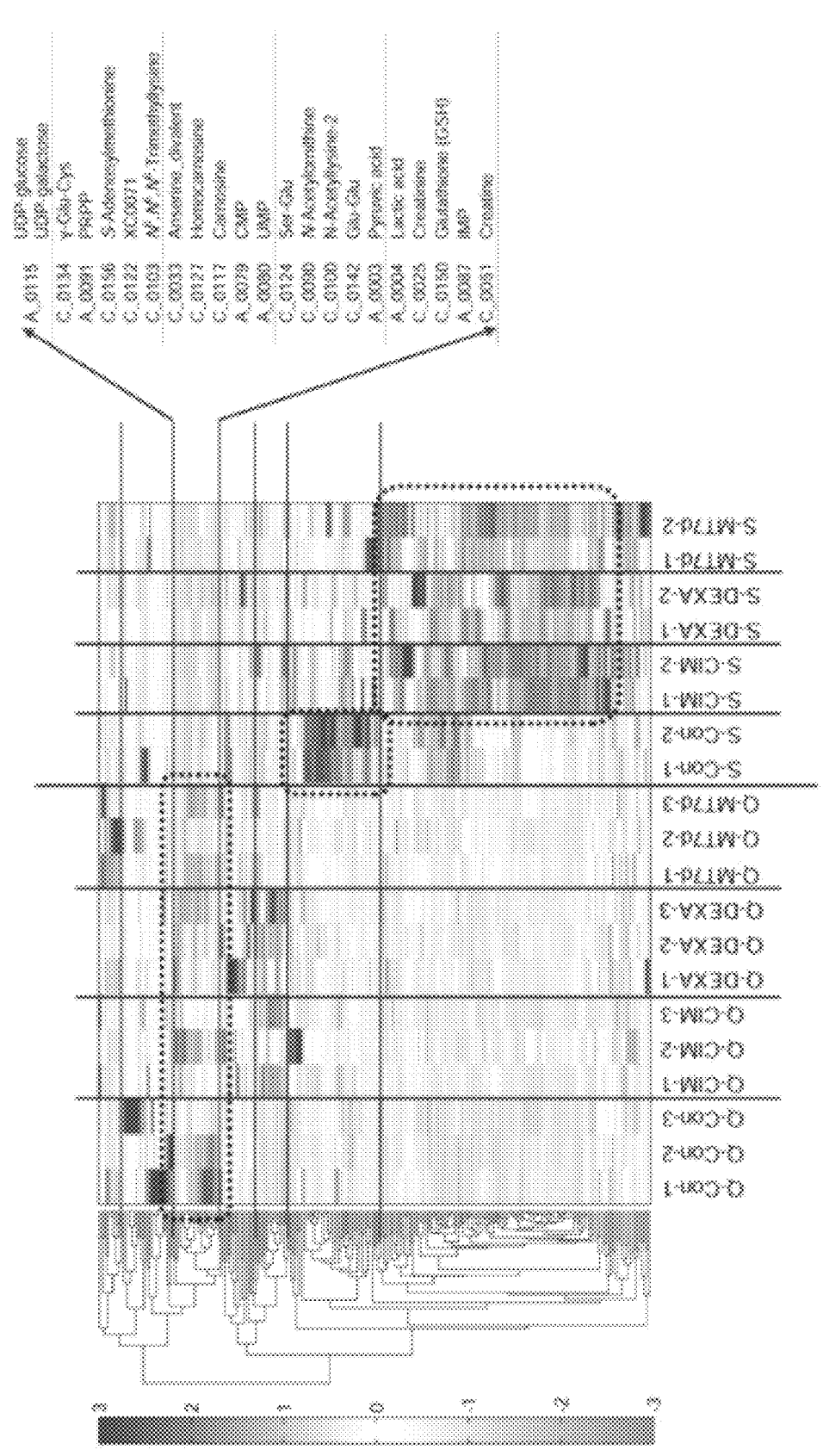
[FIG. 23]

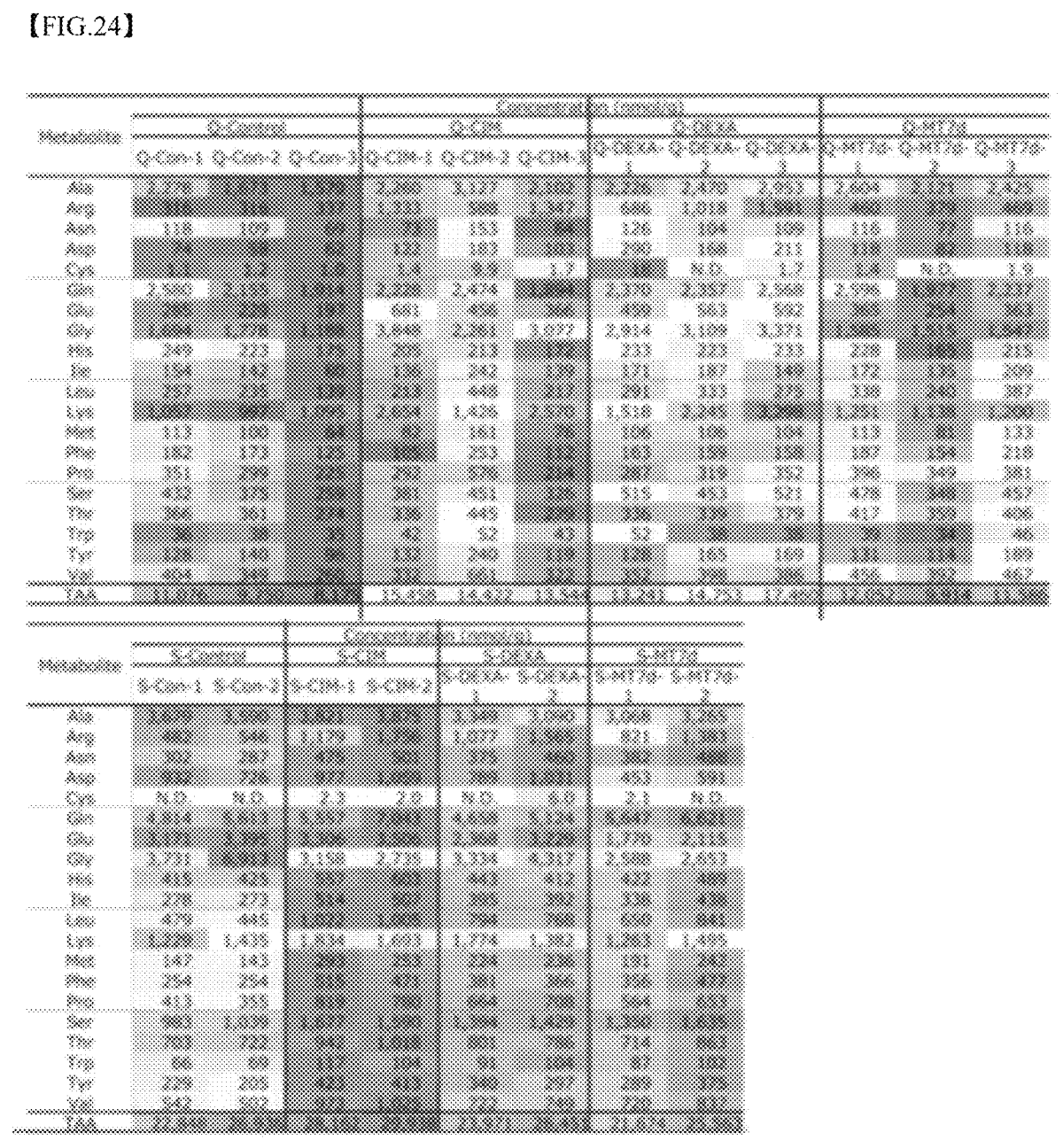

[FIG.26]
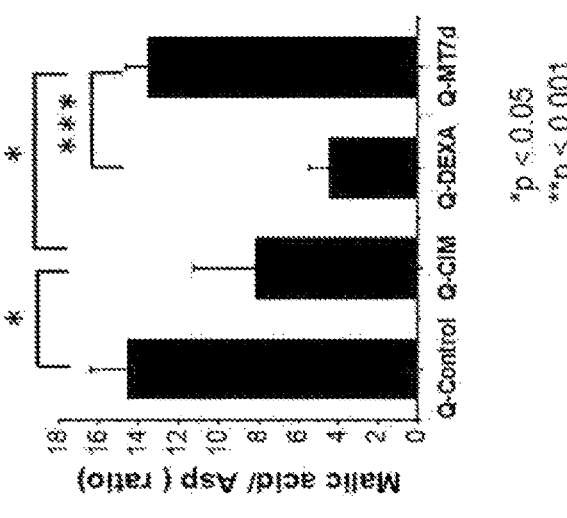
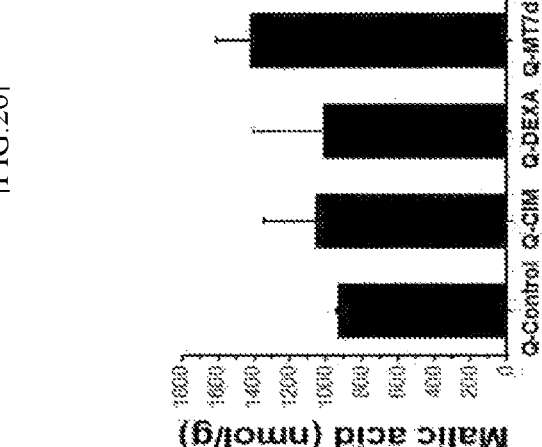
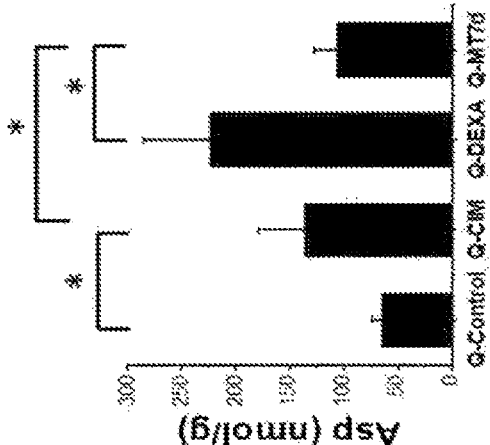

[FIG.27]
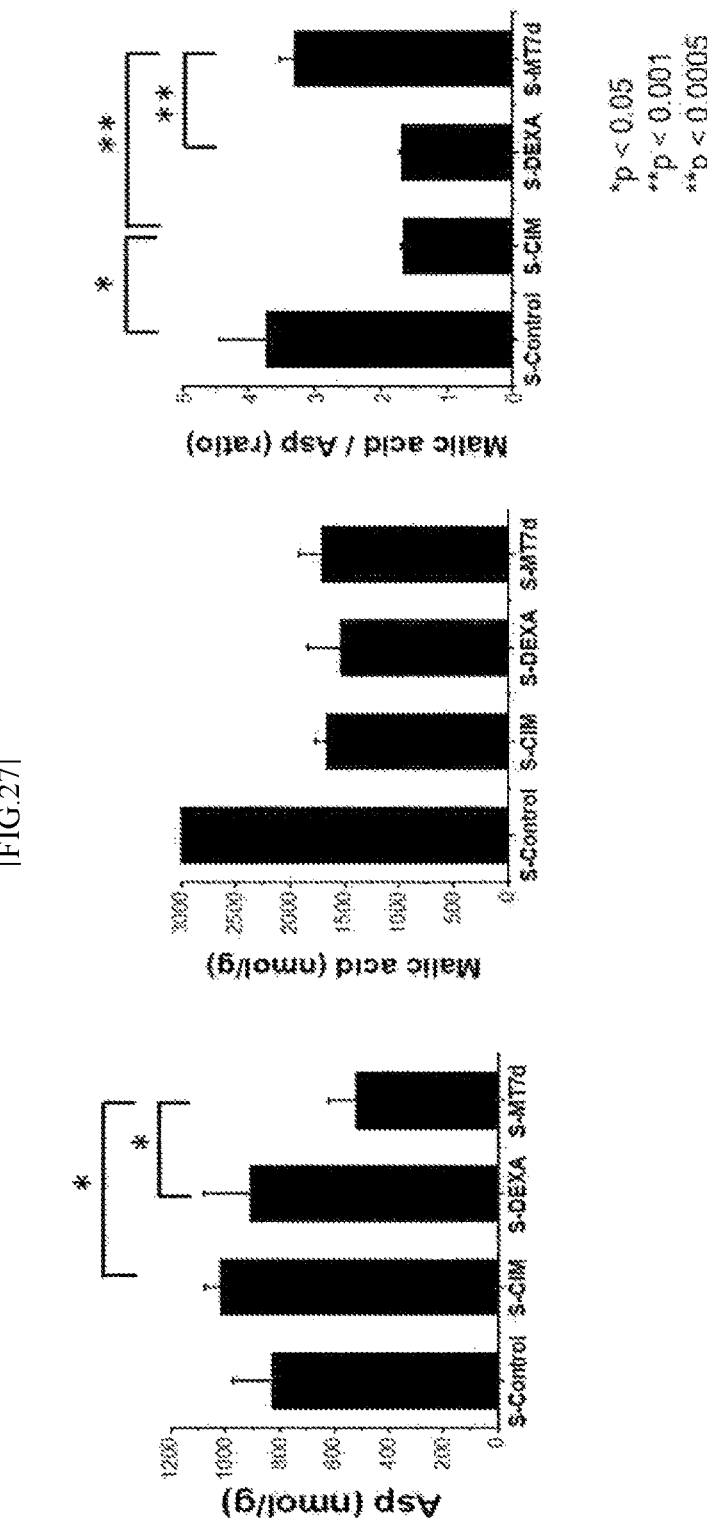

【FIG.28】
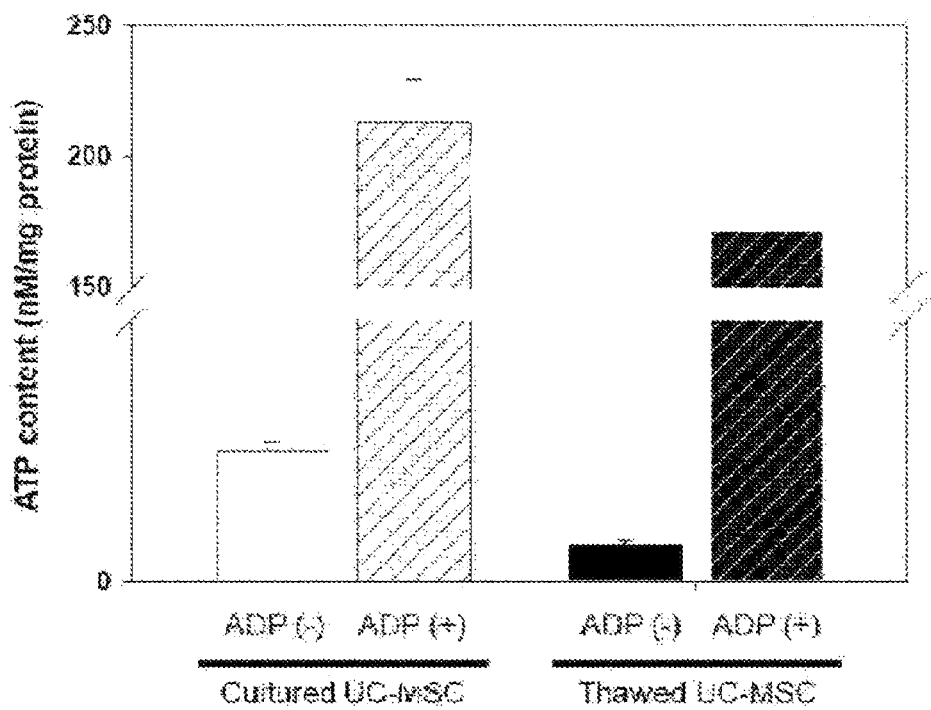
【FIG.29】
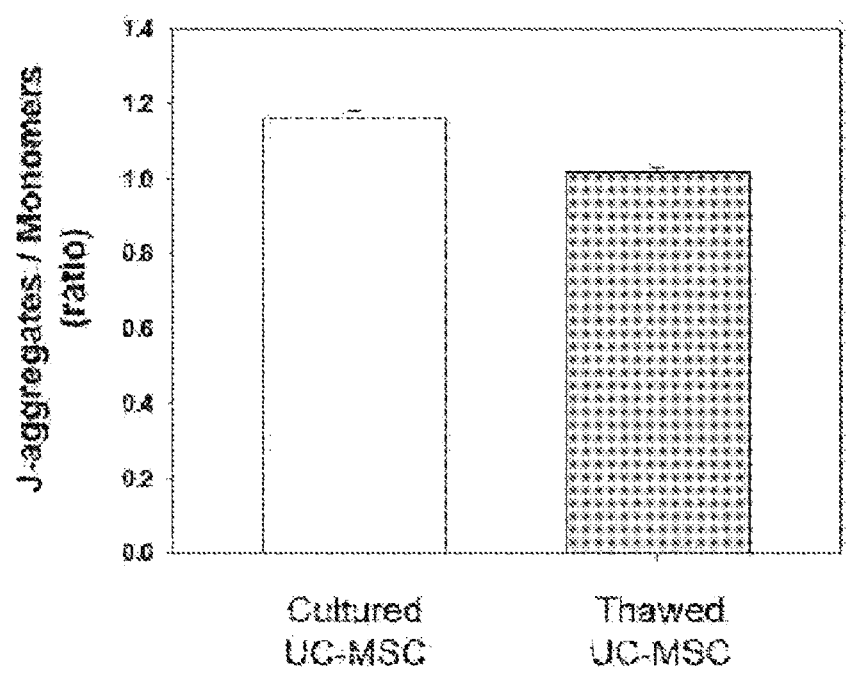

【FIG.30】
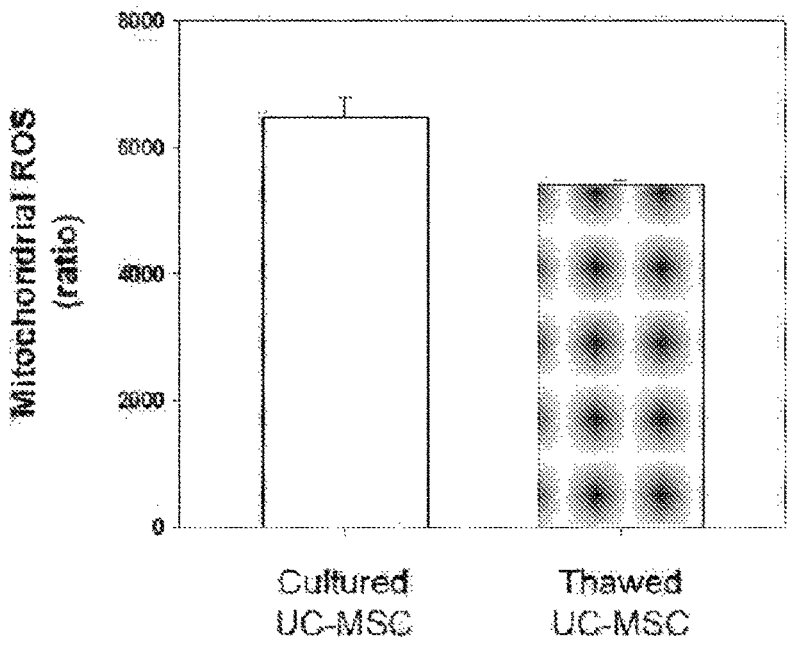
【FIG.31】
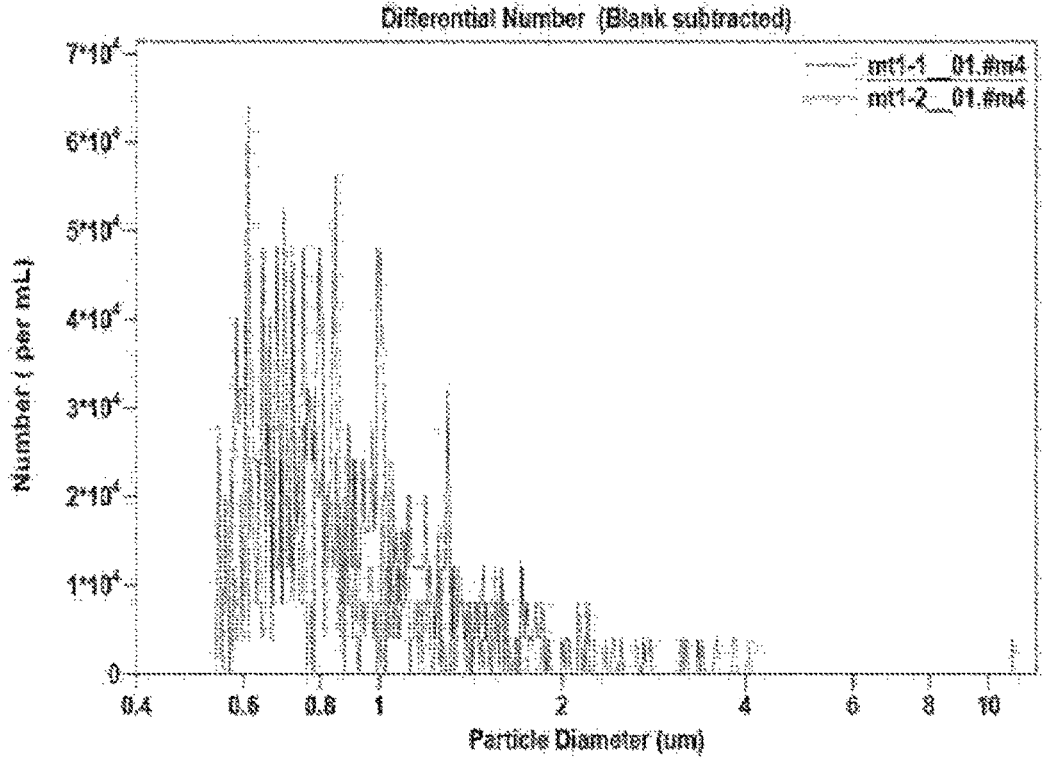

【FIG.32】
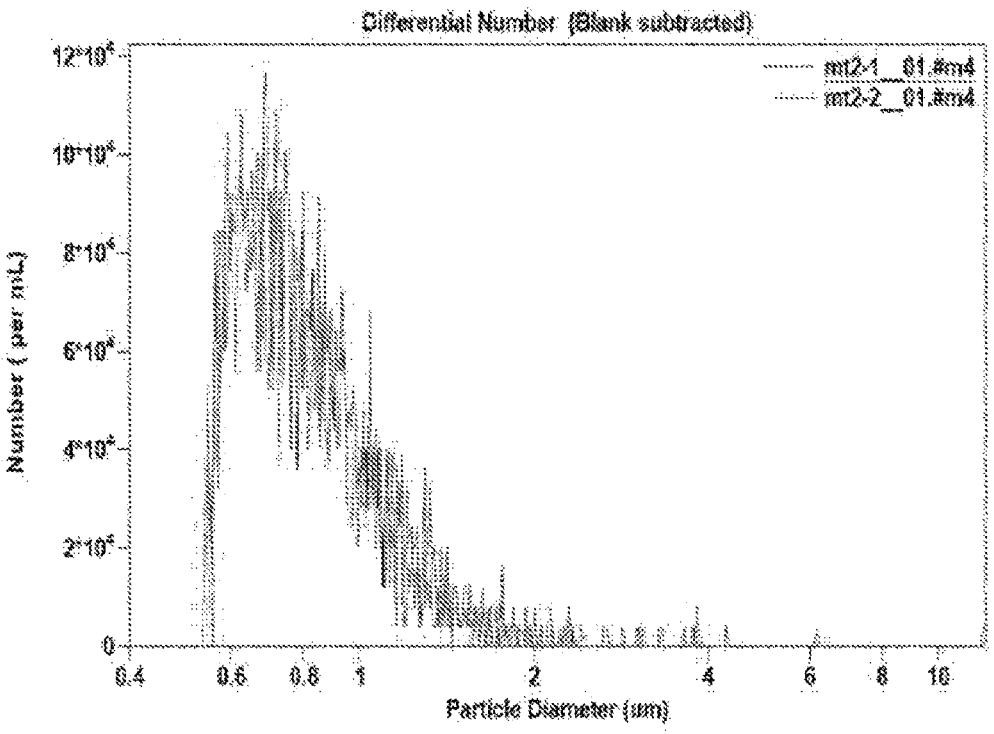
【FIG.33】
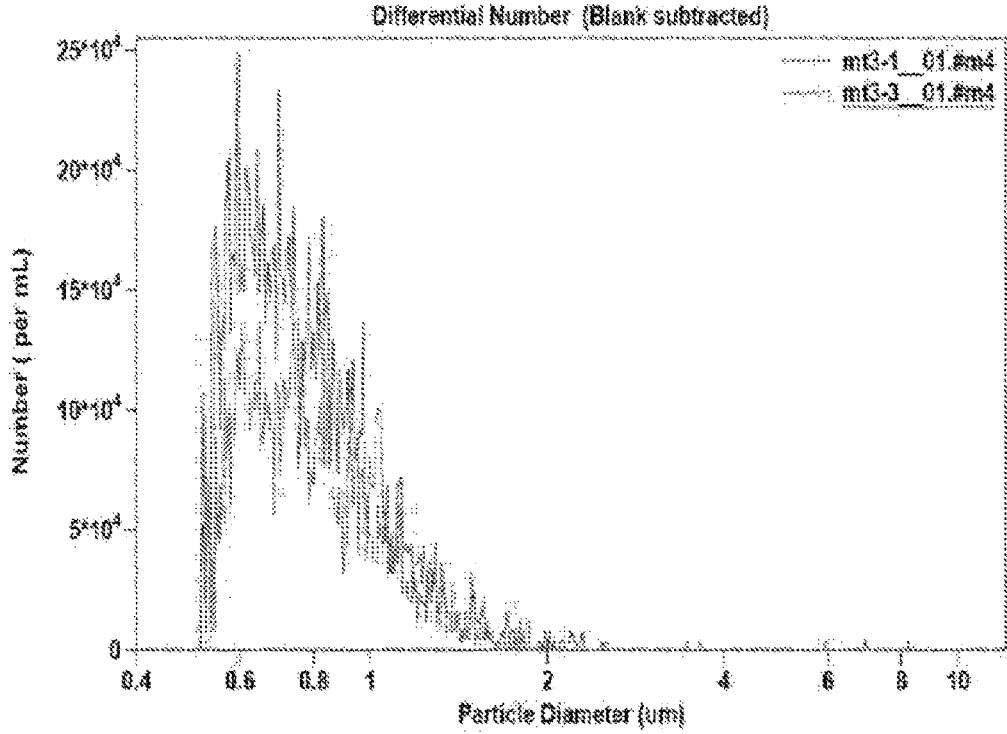

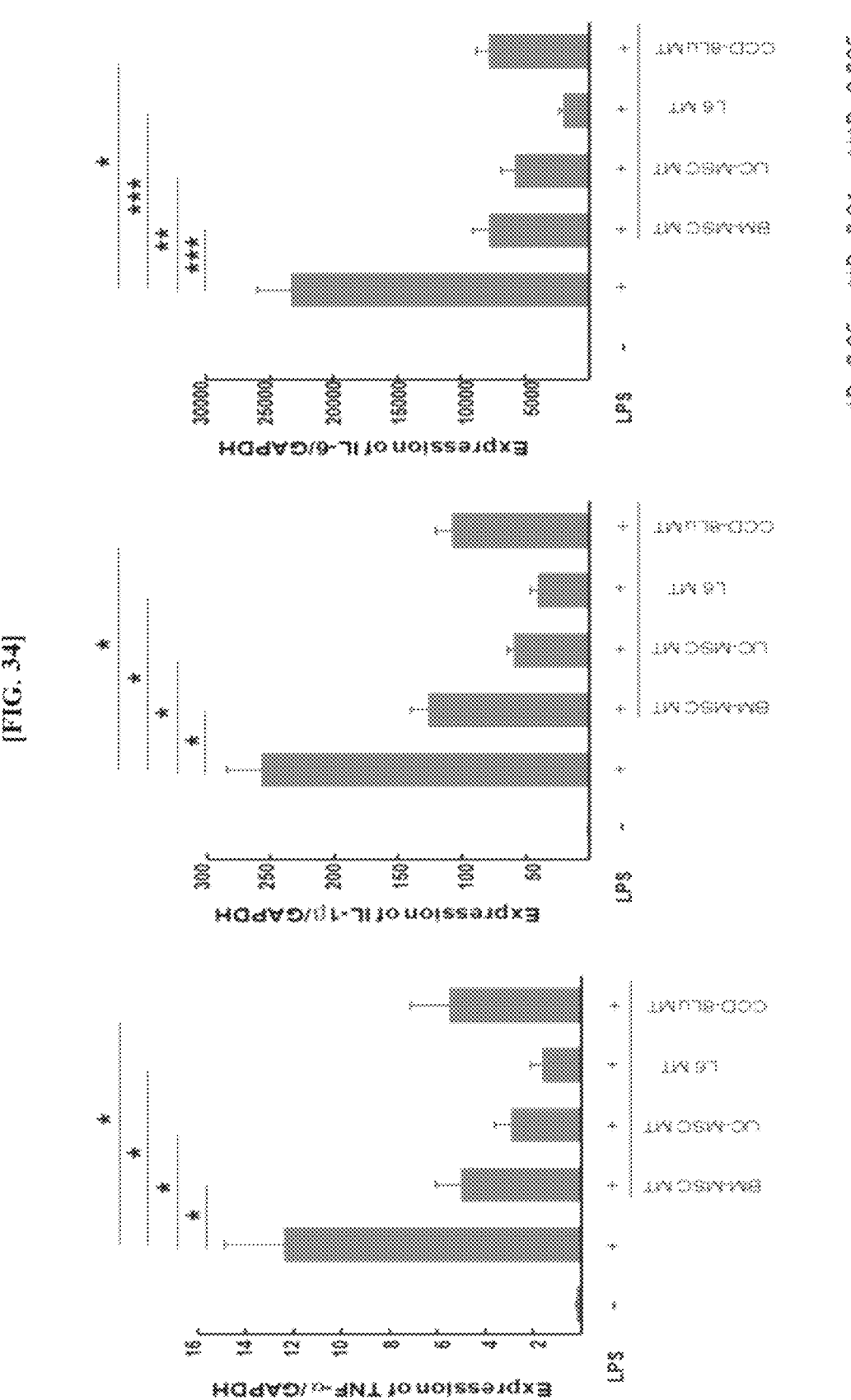
[FIG. 34]

【FIG.35】
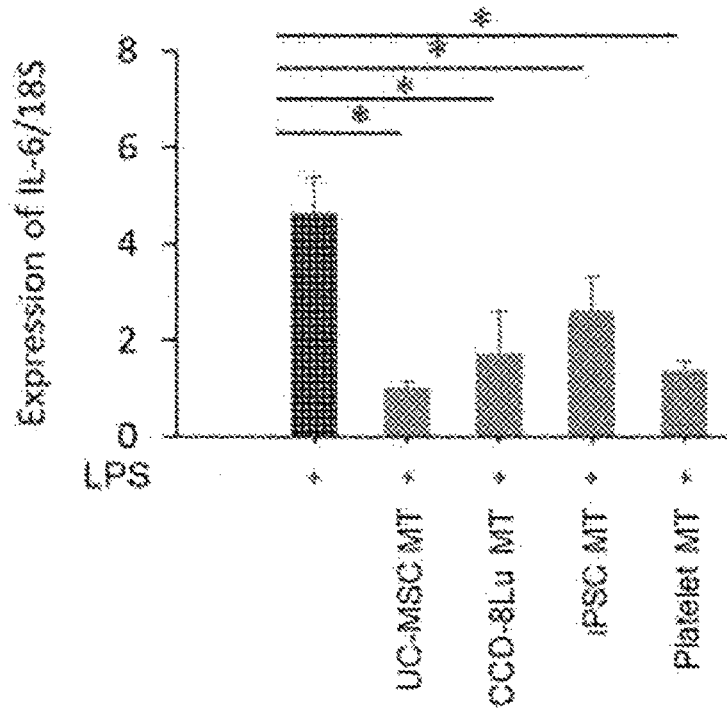
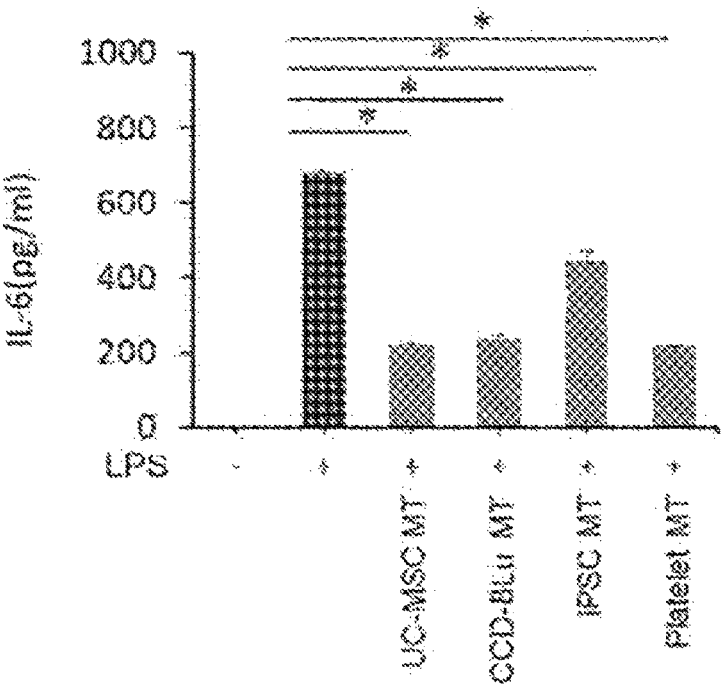

[FIG. 37]

| Name | Amount (mg) * | 50% acetonitrile in water (V/V) (uL) | Group | Dilution (Cation)** | Dilution (Anion)** | CE-MS Cation | CE-MS Anion | (253 nm) | OD/UV |
|------|------|------|------|------|------|------|------|------|------|
| Q-Con-1 | 21.4 | 450 | Q-Control | 2 | 5 | 114 | 88 | 182 | 71.9% |
| Q-Con-2 | 37.8 | 750 | | 2 | 5 | 110 | 87 | 186 | 70.4% |
| Q-Con-3 | 40.2 | 750 | | 2 | 5 | 109 | 79 | 182 | 71.9% |
| Q-CIM-1 | 32.0 | 750 | Q-CIM | 2 | 5 | 113 | 79 | 183 | 72.3% |
| Q-CIM-2 | 38.2 | 750 | | 2 | 5 | 116 | 89 | 181 | 71.9% |
| Q-CIM-3 | 33.7 | 750 | | 2 | 5 | 112 | 87 | 187 | 68.0% |
| Q-DEXA-1 | 37.3 | 750 | Q-DEXA | 2 | 5 | 122 | 79 | 191 | 74.7% |
| Q-DEXA-2 | 27.7 | 600 | | 2 | 5 | 121 | 73 | 188 | 75.5% |
| Q-DEXA-3 | 30.7 | 750 | | 2 | 5 | 120 | 88 | 189 | 72.3% |
| Q-MT7d-1 | 27.6 | 600 | Q-MT7d | 2 | 5 | 117 | 68 | 188 | 73.1% |
| Q-MT7d-2 | 38.6 | 750 | | 2 | 5 | 116 | 77 | 189 | 73.1% |
| Q-MT7d-3 | 40.8 | 750 | | 2 | 5 | 119 | 77 | 190 | 74.7% |
| S-Con-1 | 14.0 | 300 | S-Control | 2 | 5 | 121 | 89 | 189 | 78.7% |
| S-Con-2 | 9.7 | 225 | | 2 | 5 | 113 | 71 | 195 | 74.7% |
| S-CIM-1 | 7.9 | 225 | S-CIM | 2 | 5 | 125 | 69 | 195 | 76.7% |
| S-CIM-2 | 8.4 | 225 | | 2 | 5 | 109 | 79 | 195 | 77.5% |
| S-DEXA-1 | 9.2 | 225 | S-DEXA | 2 | 5 | 125 | 71 | 195 | 68.6% |
| S-DEXA-2 | 4.4 | 225 | | 2 | 5 | 110 | 69 | 195 | 75.5% |
| S-MT7d-1 | 7.1 | 225 | S-MT7d | 2 | 5 | 121 | 79 | 191 | 82.6% |
| S-MT7d-2 | 9.9 | 225 | | 2 | 5 | 132 | 77 | 191 | |
| | | | | | | 150 | 103 | | |

\* Amount of samples was measured in HMT.
\** Dilution factors for Measurement

Quadriceps muscles of Control (C57 BL6) mice (N = 3, Q-Con), c protein induced myositis (CIM) (N = 3, Q-CIM) and dexamethasone treated (DEXA) mice (N = 3, Q-DEXA) and mitochondria treated (Q-MT7d, 5ug) (N = 3, Q-CIM) were used for the metabolomic analysis (Human Metabolome Technologies Inc., Tsuruoka, Japan)

SEQUENCE LISTING

<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Synthetic IL-6-F

<400> SEQUENCE: 1
tagtccttcc taccccaatt tcc                                           23

<210> SEQ ID NO 2
<211> LENGTH: 21
<212> TYPE: DNA
<213> ORGANISM: Artificial Sequence
<220> FEATURE:
<223> OTHER INFORMATION: Synthetic IL-6-R

<400> SEQUENCE: 2
ttggtcctta gccactcctt c                                            21

<210> SEQ ID NO 3
<211> LENGTH: 23
<212> TYPE: DNA
<213> ORGANISM: Artificial Sequence
<220> FEATURE:
<223> OTHER INFORMATION: Synthetic TNF-alpha-F

<400> SEQUENCE: 3
ccctcacact cagatcatct tct                                           23

<210> SEQ ID NO 4
<211> LENGTH: 19
<212> TYPE: DNA
<213> ORGANISM: Artificial Sequence
<220> FEATURE:
<223> OTHER INFORMATION: Synthetic TNF-alpha-R

<400> SEQUENCE: 4
gctacgacgt gggctacag                                              19

<210> SEQ ID NO 5
<211> LENGTH: 20
<212> TYPE: DNA
<213> ORGANISM: Artificial Sequence
<220> FEATURE:
<223> OTHER INFORMATION: Synthetic TNF-alpha-S

<400> SEQUENCE: 5
tctcatcagt tctatggccc                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic TNF-alpha-AS

<400> SEQUENCE: 6
gggagtagac aaggtacaac                                            20

<210> SEQ ID NO 7
<211> LENGTH: 22
<212> TYPE: DNA
<213> ORGANISM: Artificial Sequence
<220> FEATURE:
<223> OTHER INFORMATION: Synthetic IL-1beta-F

<400> SEQUENCE: 7
aacctgctgg tgtgtgacgt tc                                                                       22

<210> SEQ ID NO 8
<211> LENGTH: 22
<212> TYPE: DNA
<213> ORGANISM: Artificial Sequence
<220> FEATURE:
<223> OTHER INFORMATION: Synthetic IL-1beta-R

<400> SEQUENCE: 8
cagcacgagg cttttttgtt gt                                                                       22

<210> SEQ ID NO 9
<211> LENGTH: 21
<212> TYPE: DNA
<213> ORGANISM: Artificial Sequence
<220> FEATURE:
<223> OTHER INFORMATION: Synthetic IL-6-AS

<400> SEQUENCE: 9
ctaggtttgc cgagtagatc t                                                                        21

<210> SEQ ID NO 10
<211> LENGTH: 24
<212> TYPE: DNA
<213> ORGANISM: Artificial Sequence
<220> FEATURE:
<223> OTHER INFORMATION: Synthetic IL-6-S

<400> SEQUENCE: 10
ccaaactgga tataatcagg aaat                                                                     24

<210> SEQ ID NO 11
<211> LENGTH: 19
<212> TYPE: DNA
<213> ORGANISM: Artificial Sequence
<220> FEATURE:
<223> OTHER INFORMATION: Synthetic GAPDH-S

<400> SEQUENCE: 11
ggtgaaggtc ggtgtgaag                                                                           19

<210> SEQ ID NO 12
<211> LENGTH: 20
<212> TYPE: DNA
<213> ORGANISM: Artificial Sequence
<220> FEATURE:
<223> OTHER INFORMATION: Synthetic GAPDH-AS

<400> SEQUENCE: 12
ctcgctcctg gaagatggtg                                                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic Human IL-6-S

<400> SEQUENCE: 13
ccacacagac agccactcac                                                                          20

-continued

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Human IL-6-AS

<400> SEQUENCE: 14
tttcaccagg caagtctcct                                                  20

<210> SEQ ID NO 15
<211> LENGTH: 21
<212> TYPE: DNA
<213> ORGANISM: Artificial Sequence
<220> FEATURE:
<223> OTHER INFORMATION: Synthetic Human 18S-S

<400> SEQUENCE: 15
ctcccacttg gataactgtg g                                                21

<210> SEQ ID NO 16
<211> LENGTH: 20
<212> TYPE: DNA
<213> ORGANISM: Artificial Sequence
<220> FEATURE:
<223> OTHER INFORMATION: Synthetic Human 18S-AS

<400> SEQUENCE: 16
gaccgggttg gttttgatct                                                  20
```

1

PHARMACEUTICAL COMPOSITION FOR PREVENTING OR TREATING MYOSITIS, COMPRISING ISOLATED MITOCHONDRIA AS ACTIVE INGREDIENT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 730210_403USPC_SEQUENCE LISTING.txt. The text file is 3.3 KB, was created on Oct. 27, 2021, and is being submitted electronically via EFS-Web.

TECHNICAL FIELD

The present invention relates to a pharmaceutical composition for preventing or treating myositis, comprising mitochondria as an active ingredient.

BACKGROUND ART

Myositis is a disease in which inflammation occurs in muscles and muscle fibers are damaged, leading to pain of the muscles and the reduced ability of the muscles to contract. Myositis is divided into dermatomyositis, polymyositis, and inclusion body myositis, and among them, polymyositis and dermatomyositis are inflammatory myopathies in which a symptom of a decrease in muscle strength in the extremities close to the trunk, increased muscle enzyme levels, increased inflammatory cytokine expression, abnormal electromyogram, abnormality in muscle biopsy and the like appear.

In addition, muscle weakness due to polymyositis and dermatomyositis mostly progresses gradually over several weeks or several months, but in extremely rare cases, it progresses rapidly. When severe muscle weakness is not treated, it will lead to muscle loss. It has been reported that about 15% to 30% of patients suffering from polymyositis are accompanied by malignant tumors, and when dermatomyositis occurs in older adults, cancer develops together.

Steroid, immunosuppressants, or immunomodulators are used in the treatment of polymyositis and dermatomyositis. Steroids are the most commonly used drugs for early treatment, and it is determined whether to use an immunosuppressant depending on the response to steroid treatment and side effects. About 75% of patients with myositis are prescribed with additional immunosuppressants in addition to steroids. Recently, it has been demonstrated that as an immunomodulator, immunoglobulin for intravenous administration has an effect of improving muscle strength in dermatomyositis as well as signs that are shown in muscle biopsy, and thus it is used for dermatomyositis. However, immunosuppressants and immunomodulators have disadvantages in which they are directly involved in the immune system and thus may have side effects, and the effect of the drugs does not last for a long period of time, and thus the injection of the drugs must be repeated every 6 to 8 weeks.

In addition, recently, a myositis-induced mouse model has been developed and used in the development of therapeutic agents for myositis. Specifically, in 2007, a single administration of recombinant skeletal muscle fast-type C protein is capable of inducing polymyositis in C57BL/6 mice, and the possibility of attempting to study a disease-specific treatment method for myositis was suggested (Sugihara T et al., Arthritis Rheum. 2007, 56 (4):1304-14). A myositis-induced mouse model has been used to evaluate the effects of immunosuppressants on myositis treatment against CXCL10 (C-X-C motif chemokine 10), a chemokine whose expression is increased in muscle tissues of polymyositis (Kim et al., *Arthritis Research & Therapy* 2014, 16:R126).

On the other hand, mitochondria are cellular organelles of eukaryotic cells involved in the synthesis and regulation of adenosine triphosphate (ATP), an intracellular energy source. Mitochondria are associated with various metabolic pathways in vivo, for example, cell signaling, cell differentiation, cell death, as well as control of cell cycle and cell growth.

DETAILED DESCRIPTION OF THE INVENTION

Technical Problem

Research for the treatment of myositis has been conducted, but the developed drug has a problem in which side effects occur or it needs to be periodically injected, and thus, a innovative treatment method has not been developed to date. Therefore, there is a need for continuous research and development for a safe and effective therapeutic agent for myositis.

Therefore, it is an object of the present invention to provide a pharmaceutical composition for treating myositis and a method for treating myositis using the same.

Solution to Problem

In order to solve the above problems, one aspect of the present invention provides a pharmaceutical composition for preventing or treating myositis, comprising mitochondria as an active ingredient.

Another aspect of the present invention provides a method for preventing or treating myositis, comprising a step of administering to a subject the pharmaceutical composition.

Effect of the Invention

When the pharmaceutical composition of the present invention comprising mitochondria as an active ingredient is administered to a subject suffering from myositis, inflammatory cells infiltrated into the muscle cells of the subject can be reduced. In addition, the pharmaceutical composition of the present invention can effectively reduce the expression of inflammatory cytokines of muscle tissues in which myositis is developed. Therefore, the pharmaceutical composition according to the present invention can be usefully used for preventing or treating myositis.

BRIEF DESCRIPTION OF DRAWINGS

FIG. 1 is a figure showing the measurement of a synthesized amount of ATP in mitochondria isolated from mesenchymal stem cells derived from umbilical cord.

FIG. 2 is a figure showing the measurement of the membrane potential activity in mitochondria isolated from mesenchymal stem cells derived from umbilical cord.

FIG. 3 is a figure showing the measurement of reactive oxygen species in mitochondria isolated from mesenchymal stem cells derived from umbilical cord.

FIG. 4 is a schematic diagram of a primary animal experiment plan for confirming the effect of treating myositis according to the administration of mitochondria using myositis-induced mice.

FIG. 5 is a photograph of quadriceps and hamstring muscle stained with H&E (hematoxylin & eosin) in a negative control group, a positive control group, and an experimental group administered with exogenous mitochondria in order to identify inflammatory cells infiltrated into the muscle fibers.

FIG. 6 is a figure showing the measurement and scoring of the number of the inflammatory cells infiltrated into the muscle fibers after staining quadriceps with H&E in a negative control group, a positive control group, and an experimental group administered with exogenous mitochondria.

FIG. 7 is a figure showing the concentration of IL-6 in the blood of mice in a normal group, a negative control group, a positive control group, and an experimental group administered with mitochondria.

FIG. 8 is a photograph of PET/MRI of mice in a negative control group, a positive control group, and an experimental group administered with exogenous mitochondria.

FIG. 9 shows that the activity of mitochondria was increased after the transplantation of mitochondria in myositis-induced mouse model.

FIG. 10 is a schematic diagram of a secondary animal experiment plan for confirming the effect of treating myositis according to the administration of exogenous mitochondria using myositis-induced mice.

FIG. 11 is a photograph of quadriceps stained with H&E in a negative control group, a positive control group, and an experimental group administered with exogenous mitochondria in order to identify inflammatory cells infiltrated into the muscle fibers.

Figure 12:
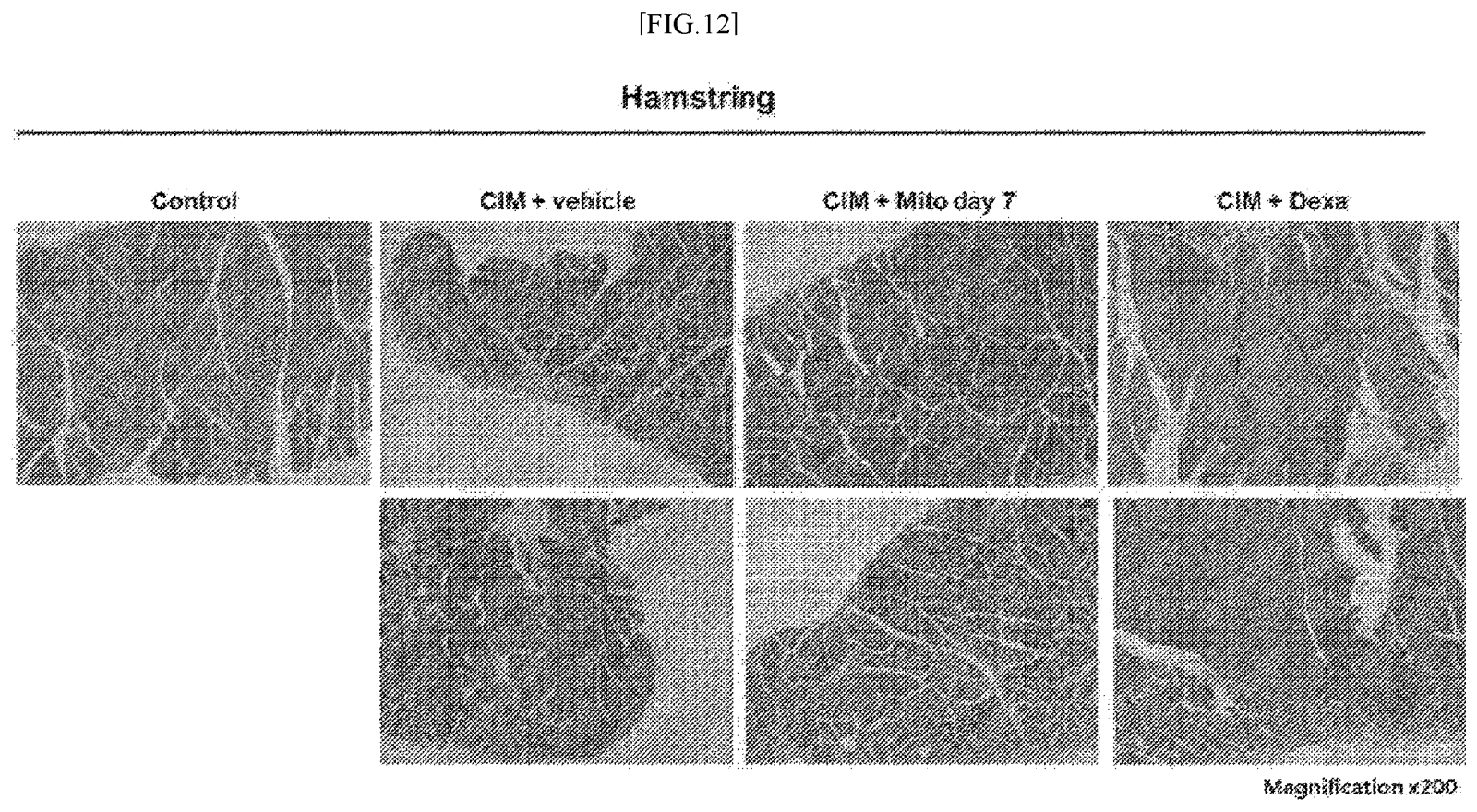

FIG. 12 is a photograph of hamstring muscle stained with H&E in a negative control group, a positive control group, and an experimental group administered with exogenous mitochondria in order to identify inflammatory cells infiltrated into the muscle fibers.

FIG. 13 is a figure showing the measurement and scoring of the number of the inflammatory cells infiltrated into the muscle fibers after staining quadriceps with H&E in a negative control group, a positive control group, and an experimental group administered with exogenous mitochondria.

FIG. 14 is a figure showing the concentration of IL-1β in the blood of mice in a normal group, a negative control group, a positive control group, and an experimental group administered with exogenous mitochondria.

FIG. 15 is a figure showing the concentration of IL-6 in the blood of mice in a normal group, a negative control group, a positive control group, and an experimental group administered with exogenous mitochondria.

FIG. 16 is a figure showing the concentration of TNF-α in the blood of mice in a normal group, a negative control group, a positive control group, and an experimental group administered with exogenous mitochondria.

FIG. 17 is a figure showing the expression amount of mRNA of IL-6 in the muscle of mice in a normal group, a negative control group, a positive control group, and an experimental group administered with exogenous mitochondria.

FIG. 18 is a schematic diagram of a tertiary animal experiment plan for confirming the effect of treating myositis according to the administration of exogenous mitochondria using myositis-induced mice.

FIG. 19 confirms that the number of inflammatory cells stained with H&E (hematoxylin & eosin) was reduced after the transplantation of mitochondria in myositis-induced mouse model.

FIG. 20 confirms that the histological score according to the scoring system was reduced after the transplantation of mitochondria in myositis-induced mouse model.

FIG. 21 shows that the number of inflammatory cytokines was reduced after the transplantation of mitochondria in myositis-induced mouse model.

FIG. 22 shows that the activity of mitochondria was increased after the transplantation of mitochondria in myositis-induced mouse model.

FIG. 23 shows the increase and decrease of the total metabolites of skeletal muscle as a result of analyzing muscle profile heat map by metabolome analysis after the transplantation of mitochondria in myositis-induced mouse model.

Figure 25:
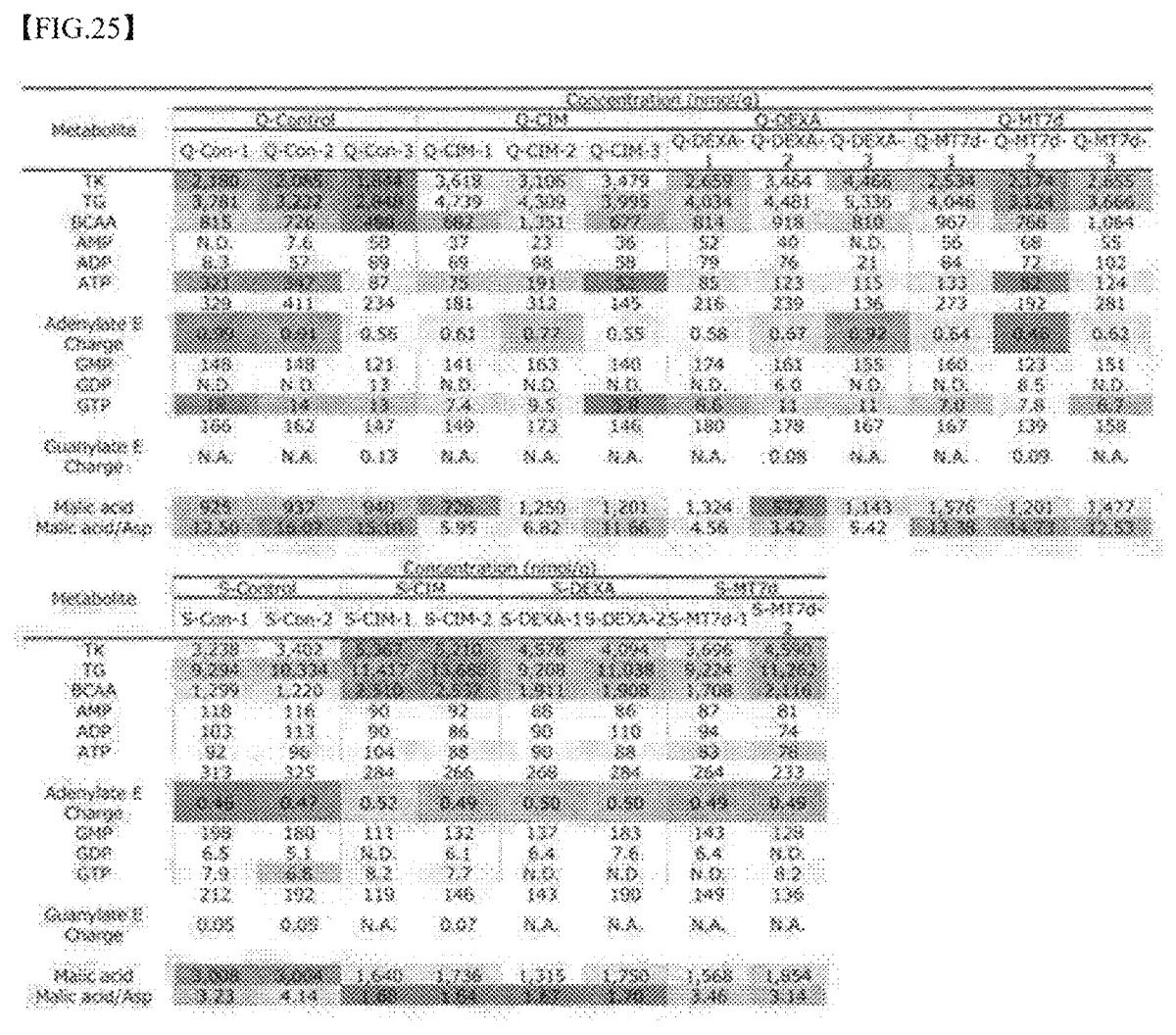

FIGS. 24 to 27 confirm that the relative quantification value ratio of malic acid and aspartate was significantly increased and recovered to the level of the control group by metabolome analysis after the transplantation of mitochondria in myositis-induced mouse model.

FIG. 28 is a figure comparing the ATP activity of mitochondria isolated from freeze-preserved mesenchymal stem cells derived from umbilical cord with that of mitochondria isolated from cultured mesenchymal stem cells derived from umbilical cord.

FIG. 29 is a figure comparing the membrane potential of mitochondria isolated from freeze-preserved mesenchymal stem cells derived from umbilical cord with that of mitochondria isolated from cultured mesenchymal stem cells derived from umbilical cord.

FIG. 30 is a figure showing the measurement of reactive oxygen species in mitochondria isolated from freeze-preserved mesenchymal stem cells derived from umbilical cord and mitochondria isolated from cultured mesenchymal stem cells derived from umbilical cord.

FIG. 31 is a figure measuring the number of mitochondria in a solution containing mitochondria in a concentration of 1 μg/mL using a particle counter (Multisizer 4e, Beckman Coulter).

FIG. 32 is a figure measuring the number of mitochondria in a solution containing mitochondria in a concentration of 2.5 μg/mL using a particle counter.

FIG. 33 is a figure measuring the number of mitochondria in a solution containing mitochondria in a concentration of 5 μg/mL using a particle counter.

FIG. 34 is a figure confirming the ability to inhibit the expression of mRNA of TNF-α, IL-1β, and IL-6 by mitochondria derived from several kinds of cells in RAW264.7 cells activated with LPS.

FIG. 35 is a figure observing the ability to inhibit the expression of mRNA of IL-6 by mitochondria derived from several kinds of cells in THP-1 cells activated with LPS.

FIG. 36 is a figure observing the ability to inhibit the expression of protein of IL-6 by mitochondria derived from several kinds of cells in THP-1 cells activated with LPS.

FIG. 37 shows the information of muscles used in metabolome analysis.

BEST MODE FOR CARRYING OUT THE INVENTION

Hereinafter, the present invention will be described in detail.

One aspect of the present invention provides a pharmaceutical composition for preventing or treating myositis, comprising mitochondria as an active ingredient.

As used herein, the term "myositis" refers to a disease in which inflammation occurs in muscles and muscle fibers are damaged. Specifically, myositis is divided into dermatomyositis, polymyositis, and inclusion body myositis, and among them, polymyositis and dermatomyositis belong to inflammatory myopathies. The expression of inflammatory cytokines or chemokines such as CXCL10, IL-1β, TNF-α, IL-6 and the like in muscle tissues of polymyositis or dermatomyositis is increased. Immunosuppressants or immunomodulators that inhibit CXCL10, IL-1β, TNF-α, or IL-6 are being developed as therapeutic agents for myositis. However, in the case of immunosuppressants or immunomodulators, there is a problem in which side effects occur due to direct involvement in immune system.

In addition, a myositis-induced mouse model may be used for the development of a therapeutic agent for myositis. The myositis-induced mouse model may be produced by intradermally injecting CFA (Complete Freund's adjuvant) containing C protein fragments and heat-killed Mycobacterium butyricum and intraperitoneally injecting PT (pertussis toxin). In this case, CD8 T cells migrate from 7 days after the injection of the drug, and infiltration into the muscle may occur to cause the inflammation. In this case, since the tissues in which inflammation and inflammatory cells are observed in the muscles of myositis patients are the quadriceps and hamstring muscle, the tissues of the quadriceps and hamstring muscle may be also used in myositis-induced mice.

Unless otherwise stated in the present specification, the term "active ingredient" refers to an ingredient that exhibits an activity alone or in combination with an adjuvant (carrier) that does not have an activity in itself.

As shown in the experimental examples, metabolomic profiles were analyzed for both quadriceps, white muscle, and soleus muscle, red muscle, using CE-TOFMS in muscle of C-protein induced myositis mouse model (CIM). In the myositis-induced group, the ratio of malate and aspartate was decreased, and based on the above, it was confirmed that there was mitochondria damage. As a result of the experiment, it was confirmed that inflammation was ameliorated and mitochondria damage was recovered in CIM mouse model by a test for confirming the potency of injection of exogenous mitochondria at several doses.

The mitochondria may be obtained from mammals, and may be obtained from humans. Specifically, the mitochondria may be isolated from cells or tissues. For example, the mitochondria may be isolated from cells cultured in vitro. In addition, the mitochondria may be obtained from somatic cells, germ cells, blood cells, or stem cells. In addition, the mitochondria may be obtained from platelets. The mitochondria may be normal mitochondria obtained from cells in which the biological activity of mitochondria is normal. In addition, the mitochondria may be cultured in vitro.

In addition, the mitochondria may be obtained from an autologous, allogenic, or xenogenic subject. Specifically, the autologous mitochondria refer to mitochondria obtained from tissues or cells of the same subject. In addition, the allogenic mitochondria refer to mitochondria obtained from a subject that belongs to the same species as the subject and has different genotypes for alleles. In addition, the xenogenic mitochondria refer to mitochondria obtained from a subject that belongs to the different species from the subject.

Specifically, the somatic cells may be muscle cells, hepatocytes, nerve cells, fibroblasts, epithelial cells, adipocytes, osteocytes, leukocytes, lymphocytes, platelets, or mucosal cells. In addition, the germ cells are cells that undergo meiosis and mitosis, and may be sperms or eggs. In addition, the stem cells may be any one selected from the group consisting of mesenchymal stem cells, adult stem cells, induced pluripotent stem cells, embryonic stem cells, bone marrow stem cells, neural stem cells, limbal stem cells, and tissue-derived stem cells. In this case, the mesenchymal stem cells may be any one selected from the group consisting of umbilical cord, umbilical cord blood, bone marrow, fat, muscle, nerve, skin, amniotic membrane, and placenta.

On the other hand, when the mitochondria are isolated from specific cells, the mitochondria can be isolated through various known methods, for example, using a specific buffer solution or using a potential difference and a magnetic field and the like.

The isolation of mitochondria may be obtained by crushing and centrifuging the cells in terms of maintaining the activity of mitochondria. In one embodiment, it may be performed by a step of culturing cells and conducting a first centrifugation of a pharmaceutical composition comprising the cells to produce pellets, a step of resuspending the pellets in a buffer solution and homogenizing the same, a step of conducting a second centrifugation of the homogenized solution to produce a supernatant, and a step of conducting a third centrifugation of the supernatant to purify the mitochondria. In this case, it is preferable in terms of maintaining cell activity that the time for which the second centrifugation is performed is regulated shorter than the time for which the first centrifugation and the third centrifugation are performed, and the speed may be increased from the first centrifugation to the third centrifugation.

Specifically, the first to third centrifugation may be performed at a temperature of 0° C. to 10° C., preferably at a temperature of 3° C. to 5° C. In addition, the time for which the centrifugation is performed may be from 1 minute to 50 minutes, and may be appropriately adjusted according to the number of centrifugation and the content of the sample and the like.

In addition, the first centrifugation may be performed at a speed of 100×g to 1,000×g, or 200×g to 700×g, or 300×g to 450×g. In addition, the second centrifugation may be performed at a speed of 1×g to 2,000×g, or 25×g to 1,800×g, or 500×g to 1,600×g. In addition, the third centrifugation may be performed at a speed of 100×g to 20,000×g, or 500×g to 18,000×g, or 800×g to 15,000×g.

The isolated mitochondria can be quantified by quantifying proteins. Specifically, the isolated mitochondria can be quantified through a BCA (bicinchoninic acid assay) analysis. In this case, the mitochondria in the pharmaceutical composition may be included in a concentration of 0.1 µg/mL to 1,000 µg/mL, 1 µg/mL to 750 µg/mL, or 25 µg/mL to 500 µg/mL. In one example of the present invention, it was used in a concentration of 25 µg/mL, 50 µg/mL, and 100 µg/mL.

In addition, the number of the isolated mitochondria may be measured through a particle counter (Multisizer 4e, Beckman Coulter), and the number of mitochondria may be as shown in Table 1 below with reference to a paper written by James D. McCully (*J Vis Exp.* 2014; (91): 51682).

TABLE 1

| Amount of Isolated Mitochondria (µg) | Number of Mitochondria | Concentration (µg/mℓ) |
|---|---|---|
| 0.01 | $2.16 \times 10^5 \pm 0.01 \times 10^5$ | 0.1 |
| 1 | $2.16 \times 10^7 \pm 0.08 \times 10^7$ | 10 |
| 25 | $0.54 \times 10^9 \pm 0.02 \times 10^9$ | 250 |
| 50 | $1.08 \times 10^9 \pm 0.04 \times 10^9$ | 500 |
| 100 | $2.16 \times 10^9 \pm 0.08 \times 10^9$ | 1,000 |

As shown in Example 9 of the present invention, as a result of measuring the number of mitochondria in a concentration of 1 μg/mL, 2.5 μg/mL, and 5 μg/mL using a particle counter, it was measured as $1.96\times10^6\pm0.98\times10^6$, $5.97\times10^6\pm0.19\times10^6$, and $1.01\times10^7\pm0.32\times10^7$. As compared to Table 1 above, it was confirmed that the number of mitochondria in a concentration of 10 μg/mL is $2.16\times10^7\pm0.08\times10^7$, which is similar to $2.02\times10^7\pm0.64\times10^7$ obtained from multiplying by 2 times the number of mitochondria in a concentration of 5 μg/mL. In this case, the mitochondria in the pharmaceutical composition may be included at a content of $1\times10^5$ mitochondria/mL to $5\times10^9$ mitochondria/mL. Specifically, the mitochondria in the pharmaceutical composition may be included at a content of $1\times10^5$ mitochondria/mL to $5\times10^9$ mitochondria/mL, $2\times10^5$ mitochondria/mL to $2\times10^9$ mitochondria/mL, $5\times10^5$ mitochondria/mL to $1\times10^9$ mitochondria/mL, $1\times10^6$ mitochondria/mL to $5\times10^8$ mitochondria/mL, $2\times10^6$ mitochondria/mL to $2\times10^8$ mitochondria/mL, $5\times10^6$ mitochondria/mL to $1\times10^8$ mitochondria/mL, or $1\times10^7$ mitochondria/mL to $5\times10^7$ mitochondria/mL. The pharmaceutical composition may include the mitochondria in the concentration and content of the above range, and thus it is easy to regulate the dose of mitochondria upon administration, and the degree of the improvement of myositis symptoms in patients can be further enhanced.

In particular, the therapeutically effective dose of mitochondria comprised in the pharmaceutical composition may be $3\times10^5$ mitochondria/kg to $1.5\times10^{10}$ mitochondria/kg as one dose based on the body weight of the subject to be administered. Specifically, the therapeutically effective dose of mitochondria comprised in the pharmaceutical composition may be $3\times10^5$ mitochondria/kg to $1.5\times10^{10}$ mitochondria/kg, $6\times10^5$ mitochondria/kg to $6\times10^9$ mitochondria/kg, $1.5\times10^6$ mitochondria/kg to $3\times10^9$ mitochondria/kg, $3\times10^6$ mitochondria/kg to $1.5\times10^9$ mitochondria/kg, $6\times10^6$ mitochondria/kg to $6\times10^8$ mitochondria/kg, $1.5\times10^7$ mitochondria/kg to $3\times10^8$ mitochondria/kg or $3\times10^7$ mitochondria/kg to $1.5\times10^8$ mitochondria/kg as one dose based on the body weight of the subject to be administered. That is, it is most preferable in terms of cell activity that the pharmaceutical composition comprising the mitochondria is administered in the range of the above-mentioned dose of mitochondria to be administered based on the body weight of the subject with myositis.

In addition, the pharmaceutical composition may be administered 1 to 10 times, 3 to 8 times, or 5 to 6 times, and preferably may be administered 5 times. In this case, the administration interval may be 1 to 7 days or 2 to 5 days, preferably 3 days.

In addition, the pharmaceutical composition according to the present invention may be administered to humans or other mammals predisposed to myositis or suffering from such diseases or disorders. In addition, the pharmaceutical composition may be an injection that may be administered intravenously, intramuscularly, or subcutaneously, and preferably may be an injectable preparation.

Therefore, the pharmaceutical composition according to the present invention may be manufactured as an injection that is very stable physically or chemically by adjusting the pH using a buffer solution such as an acidic aqueous solution or phosphate, which can be used in an injection, in order to secure product stability according to the distribution of an injection that is prescribed.

Specifically, the pharmaceutical composition of the present invention may comprise water for injection. The water for injection refers to distilled water made to dissolve a solid injection or to dilute a water-soluble injection.

In addition, the pharmaceutical composition of the present invention may comprise a stabilizer or a solubilizing agent. For example, the stabilizer may be pyrosulfite, citric acid, or ethylenediaminetetraacetic acid, and the solubilizing agent may be hydrochloric acid, acetic acid, sodium hydroxide, sodium hydrogen carbonate, sodium carbonate, or potassium hydroxide.

In another aspect of the present invention, the present invention provides a method for preventing or treating myositis, comprising a step of administering to a subject the pharmaceutical composition as described above. Herein, the subject may be a mammal, and preferably may be a human.

In this case, the administration may be intravenous, intramuscular, or intradermal administration. Thus, the pharmaceutical composition according to the present invention can supply exogenous mitochondria having normal activity to the veins of a subject suffering from myositis, and thus, it can be useful for increasing the activity of cells with reduced mitochondrial function or for regenerating cells with abnormal mitochondrial function and can be used for preventing or treating myositis.

In another aspect of the present invention, the present invention provides the use of isolated mitochondria for preventing or treating myositis. The details of mitochondria and myositis are as described above.

Mode for Carrying out the Invention

Hereinafter, preferred examples are presented in order to help the understanding of the present invention. However, the following examples are only provided to more easily understand the present invention, and the contents of the present invention are not limited by the following examples.

I. Preparation of Composition Comprising Mitochondria

Preparation Example 1. Preparation I of Composition Comprising Mitochondria Isolated from Mesenchymal Stem Cells Derived from Human Umbilical Cord Mesenchymal stem cells derived from human umbilical cord were inoculated into an Alpha-MEM (Alpha-Minimum Essential Medium) medium containing 10% (v/v) fetal bovine serum (FBS, Gibco), 100 μg/mL streptomycin, and 100 U/mL ampicillin and cultured for 72 hours. After the culture was completed, washing was performed twice using DPBS (Dulbecco's phosphate buffered saline, Gibco). The washed cells were treated with 0.25% (v/v) Trypsin-EDTA (TE, Gibco) to obtain the cells.

In order to isolate the mitochondria, the obtained cells were recovered in a concentration of $1\times10^7$ cells/mL using a hemocytometer. The cell line was subjected to the first centrifugation at a speed of 350×g for 10 minutes at a temperature of 4° C. At this time, the obtained pellet was recovered, resuspended in a buffer solution, and then subjected to the homogenization for 10 to 15 minutes. Thereafter, the composition containing the pellet was subjected to the second centrifugation at a speed of 1,100×g for 3 minutes at a temperature of 4° C. to obtain a supernatant. The supernatant was subjected to the third centrifugation at a speed of 12,000×g for 15 minutes at a temperature of 4°

C. to isolate the mitochondria from the cell line. The mitochondria thus obtained were mixed with PBS and then filled in a syringe.

Preparation Example 2. Preparation II of Composition Comprising Mitochondria Isolated from Mesenchymal Stem Cells Derived from Human Umbilical Cord Mesenchymal stem cells derived from human umbilical cord (UC-MSC) were inoculated into an Alpha-MEM (Alpha-Minimum essential medium, Gibco) medium containing 10% fetal bovine serum (FBS, Gibco), 100 μg/mL streptomycin, and 100 U/mL ampicillin and cultured for 72 hours. After the culture of the cells was completed, washing was performed twice using DPBS. Thereafter, the cells were obtained by treating with 0.25% Trypsin/EDTA. After the cells were resuspended so that the concentration of the cells was $1 \times 10^7$ cells/mL, the cells were subjected to the first centrifugation at a speed of 350×g for 10 minutes at a temperature of 4° C.

The washed cells were refloated using a mitochondria isolation solution and then crushed using a 1 ml syringe. Thereafter, the solution containing the crushed cells was centrifuged at 1,500×g for 5 minutes at 4° C. to remove impurities, and the supernatant containing mitochondria was recovered. The recovered supernatant was centrifuged at 20,000×g for 5 minutes at 4° C. to recover the precipitated mitochondria, and the isolated mitochondria were floated in a Tris buffer and used for the experiment after quantifying the protein by BCA method.

Preparation Example 3. Preparation of Composition Comprising Mitochondria Isolated from Mesenchymal Stem Cells Derived from Human Bone Marrow Mesenchymal stem cells derived from human bone marrow (BM-MSC) were inoculated into a DMEM (Gibco) medium containing 10% fetal bovine serum (FBS, Gibco), 100 μg/mL streptomycin, and 100 U/mL ampicillin and cultured for 72 hours.

After the culture of the cells was completed, the mitochondria were recovered and quantified as in the method described in Preparation Example 2, and then used in the experiment.

Preparation Example 4. Preparation of Composition Comprising Mitochondria Isolated from Human Fibroblasts Human fibroblasts (CCD-8LU, ATCC) were inoculated into a DMEM (Gibco) medium containing 10% fetal bovine serum (FBS, Gibco), 100 μg/mL streptomycin, and 100 U/mL ampicillin and cultured for 72 hours.

After the culture of the cells was completed, the mitochondria were recovered and quantified as in the method described in Preparation Example 2, and then used in the experiment.

Preparation Example 5. Preparation of Composition Comprising Mitochondria Isolated from Human Induced Pluripotent Stem Cells Human induced pluripotent stem cells (iPSC) were cultured in a TeSR™-E8™ (stem cell 05990) medium in a cell culture container coated with 10 μg/ml of vitronectin (stem cell 07180) and then used.

After the culture of the cells was completed, the mitochondria were recovered and quantified as in the method described in Preparation Example 2, and then used in the experiment.

Preparation Example 6. Preparation of Composition Comprising Mitochondria Isolated from Platelets Mitochondria In order to isolate mitochondria from platelets, the porcine whole blood was centrifuged at 500×g for 3 minutes at ambient temperature, and then the supernatant containing platelet-rich plasma (PRP) was recovered. The recovered supernatant was centrifuged at 1,500×g for 5 minutes to remove the supernatant, and the precipitate containing platelets was recovered. The concentrated platelet precipitate was refloated using PBS and then centrifuged at 1,500×g for 5 minutes and washed. The washed platelets were refloated using a mitochondria isolation solution and then crushed using a 1 ml syringe. Thereafter, the solution containing the crushed platelets was centrifuged at 1,500×g for 5 minutes at 4° C. to remove impurities, and the supernatant containing mitochondria was recovered. The recovered supernatant was centrifuged at 20,000×g for 5 minutes at 4° C. to recover the precipitated mitochondria, and the isolated mitochondria were floated in a Tris buffer and used for the experiment after quantifying the protein.

Preparation Example 7. Preparation of Composition Comprising Mitochondria Isolated from Myoblasts Derived from Skeletal Muscle of Rat L6 cells (American Type Culture Collection, ATCC, CRL-1458), a myoblast cell line derived from skeletal muscle of rats, were inoculated into a DMEM-High glucose (Dulbecco's modified eagle's medium-High glucose, Gibco) medium containing 10% fetal bovine serum (FBS, Gibco) and cultured for 72 hours.

After the culture of the cells was completed, the mitochondria were recovered and quantified as in the method described in Preparation Example 2, and then used in the experiment.

II. Confirmation of Property of Mitochondria

Example 1. Confirmation of Mitochondrial ATP Synthesis

In order to confirm whether the mitochondria isolated in Preparation Example 1 normally synthesize ATP, the mitochondrial protein concentration of the isolated mitochondria was quantified through the BCA (bicinchoninic acid assay) analysis to prepare 5 μg of mitochondria. Thereafter, the amount of ATP was quantified using a CellTiter-Glo luminescence kit (Promega, Madison, WI) according to the manufacturer's manual.

Specifically, as an experimental group, 5 μg of the prepared mitochondria was mixed in 100 μL of PBS and then dispensed in a 96-well plate. In addition, as a control group, 100 of PBS without mitochondria was dispensed in a 96-well plate. Thereafter, each well was treated with 100 μL of test solution comprised in the CellTiter-Glo luminescence kit, and then reacted in a stirrer for 2 minutes and mixed well. Thereafter, it was reacted at ambient temperature for 10 minutes, and then the absorbance was measured at a wavelength of 560 nm using a luminescence microplate reader.

As a result, it was confirmed that the amount of ATP in the experimental group containing mitochondria was greater by about 3 times or more than the amount of ATP in the control group (FIG. 1). From the above, it was confirmed that the mitochondria isolated in Preparation Example 1 normally synthesized ATP.

Example 2. Measurement of Membrane Potential of Mitochondria

In order to measure the membrane potential of the mitochondria isolated in Preparation Example 1, the mitochondrial protein concentration of the isolated mitochondria was quantified through the BCA to prepare 5 µg of mitochondria. The membrane potential of the mitochondria was measured using a JC-1 (molecular probes, cat no.1743159) dye.

Specifically, as an experimental group, 5 µg of the prepared mitochondria was mixed in 50 µL of PBS and then dispensed in a 96-well plate. In addition, as a control group, 50 µL of PBS without mitochondria was dispensed in a 96-well plate. In addition, as an additional experimental group, 5 µg of mitochondria was mixed in 50 µL of CCCP (R&D systems, CAS 555-60-2), then reacted at room temperature for 10 minutes, and then dispensed in a 96-well plate. In this case, CCCP is an ion transporter of mitochondria and depolarizes the membrane potential of mitochondria, thereby inhibiting the function of mitochondria.

Thereafter, each well was treated and reacted with the JC-1 dye so that the concentration was 2 µM, and then the absorbance was measured using a fluorescence microplate reader. At this time, the JC-1 dye is present as a monomer at a low concentration and thus shows green fluorescence, and at a high concentration, the JC-1 dye aggregates and thus shows red fluorescence (Monomer: Ex 485/Em 530, J-aggregate: Ex 535 nm/Em 590 nm). The membrane potential of mitochondria was analyzed by calculating the ratio of the absorbance of green fluorescence to the absorbance of red fluorescence.

As a result, the high membrane potential activity was shown in the experimental group containing mitochondria. On the other hand, the low membrane potential activity was shown in the additional experimental group in which mitochondria was treated with CCCP (FIG. 2). From the above, it was confirmed that the mitochondria isolated in Preparation Example 1 showed the normal membrane potential activity.

Example 3. Measurement of Reactive Oxygen Species in Mitochondria

In order to confirm the damage of the mitochondria isolated in Preparation Example 1, the mitochondrial protein concentration of the isolated mitochondria was quantified through the BCA to prepare 5 µg of mitochondria. The mitochondrial reactive oxygen species (ROS) in the mitochondria was measured using a MitoSOX red indicator (Invitrogen, cat no. M36008) dye.

Specifically, as an experimental group, 5 µg of the prepared mitochondria was mixed in 50 µL of PBS and then dispensed in a 96-well plate. In addition, as a control group, 50 µL of PBS without mitochondria was dispensed in a 96-well plate. Thereafter, the MitoSOX red indicator dye was mixed in 50 µL of PBS so that the concentration was 10 µM, and then each well was treated with the mixture and reacted for 20 minutes in an incubator in a condition of 37° C. and 5% $CO_2$. After the reaction was completed, the absorbance was measured using a fluorescence microplate reader (Ex 510 nm/Em 580 nm). As a result, it was confirmed that the mitochondrial reactive oxygen species in the mitochondria was low in both the control group and the experimental group (FIG. 3). From the above, it was confirmed that there was no damage of the mitochondria isolated in Preparation Example 1.

III. Confirmation of Effect of Mitochondria on Treatment of Myositis In Vivo

Example 4. Confirmation of Effect on Treatment of Myositis According to Administration of Exogenous Mitochondria in Myositis-Induced Mouse Model: Primary Experiment

Example 4.1. Construction of Myositis-Induced Mouse Model and Administration of Mitochondria (n=3)

CFA (Complete Freund's adjuvant) containing 200 µg of C protein fragments and 100 µg of heat-killed Mycobacterium butyricum was intradermally injected into C57BL/6 female 8-week-old mice, and 2 µg of PT (pertussis toxin) was intraperitoneally injected.

A group in which intravenous single administration of the mitochondria isolated in Preparation Example 1 (5 µg) on day 1 or day 7 after the induction of myositis was performed was set as an experimental group. In addition, a group in which intraperitoneal administration of 100 µL of PBS was performed was set as a negative control group, and a group in which intraperitoneal administration of dexamethasone at a daily dose of 0.8 mg/kg from day 1 to day 14 after the induction of myositis was performed was set as a positive control group (FIG. 4).

Example 4.2. Confirmation of Muscle Fibers into Which Inflammation was Infiltrated The mice of each group of Example 4.1 were sacrificed on day 14, and the tissues of the quadriceps and hamstring muscle were collected and stained with H&E (hematoxylin & eosin), and then the infiltration of inflammatory cells was observed with an optical microscope.

As a result, it was confirmed that the number of the inflammatory cells infiltrated into the muscle fibers in the positive control group and the experimental group was reduced as compared to the negative control group (FIG. 5). In addition, the mice of each group were sacrificed on day 14, and the tissues of the quadriceps and hamstring muscle were collected and stained with H&E, and then the number of muscle fibers into which inflammatory cells were infiltrated was evaluated using a scoring system. The score measurement method of the scoring system is shown in Table 2 below. In this case, the average values of the right and left muscles of the quadriceps and hamstring muscle were compared.

TABLE 2

| Score | Evaluation Method (Number of Inflammation-Infiltrated Muscle Fibers) |
|---|---|
| 1 | 1 muscle fiber into which inflammation was infiltrated was observed |
| 2 | 2 to 5 muscle fibers into which inflammation was infiltrated were observed |
| 3 | 6 to 15 muscle fibers into which inflammation was infiltrated were observed |

TABLE 2-continued

| Score | Evaluation Method (Number of Inflammation-Infiltrated Muscle Fibers) |
|---|---|
| 4 | 16 to 30 muscle fibers into which inflammation was infiltrated were observed |
| 5 | 30 to 99 muscle fibers into which inflammation was infiltrated were observed |
| 6 | 100 or more muscle fibers into which inflammation was infiltrated were observed |

As a result, the score of the muscle fibers into which inflammation was infiltrated in the positive control group and the experimental group was reduced as compared to the negative control group (FIG. 6).

Example 4.3. Confirmation of Concentration of Cytokine in Blood

In order to confirm the concentration of IL-6 in the blood of normal mice and mice of each group of Example 4.1 on day 14, serum was isolated from the blood of mice of each group, and then the concentration of IL-6 in the blood was measured using an IL-6 ELISA Kit (R&D Systems, MN, USA) according to the manufacturer's manual.

As a result, it was confirmed that the concentration of IL-6 in the blood was increased in the control group, whereas the concentration of IL-6 in the blood was reduced in the positive control group and the experimental group (FIG. 7).

Example 4.4. Confirmation of Inflammatory Response Through PET/MRI Analysis

First, in order to increase the glucose ingestion efficiency in the tissues of mice of each group of Example 4.1, the food was not fed from 8 hours before imaging. After 8 hours, 200 uci $^{18}$F-FDG (Cyclotron Room, Department of Nuclear Medicine, Seoul National University Hospital) was injected through the vein of the mice, and PET/MR images were taken after 1 hour.

As a result, strong radionuclide signals were observed in the legs of the mice of the negative control group. The $^{18}$F-FDG radiopharmaceutical is mostly ingested selectively in macrophages, which are inflammatory cells. Therefore, the inflammatory response could be easily monitored through a nuclear medicine imaging technology (FIG. 8).

Example 4.5. Confirmation of Change in Expression of Oxidative Phosphorylation Complex of Mitochondria The expression of oxidative phosphorylation complex II in the quadriceps in the negative control group (CIM) was reduced as compared to the control group, and the expression in the experimental group (CIM+Mito day 7) was increased as compared to the positive control group (DEXA). The expression of TOM20 in the soleus muscle in the negative control group (CIM) was reduced as compared to the control group, and the expression in the experimental group (CIM+Mito day 1, CIM+Mito day 7) was increased as compared to the positive control group (DEXA) (FIG. 9).

Taking the experimental results of Examples 4.2 to 4.5 above into consideration, the secondary experiment was conducted by setting the time point of administration of mitochondria as day 7 after the induction of myositis.

Example 5. Confirmation of Effect on Treatment of Myositis According to Administration of Exogenous Mitochondria in Myositis-Induced Mouse Model: Secondary Experiment

Example 5.1. Construction of Myositis-Induced Mouse Model and Administration of Mitochondria (n=10)

CFA containing 200 μg of C protein fragments and 100 μg of heat-killed Mycobacterium butyricum was intradermally injected into C57BL/6 female 8-week-old mice, and 2 μg of PT was intraperitoneally injected.

A group in which intravenous single administration of the mitochondria isolated in Preparation Example 1 (5 μg) on day 7 after the induction of myositis was performed was set as an experimental group. In addition, a group in which intraperitoneal administration of 100 μL of PBS was performed was set as a negative control group, and a group in which intraperitoneal administration of dexamethasone at a daily dose of 0.8 mg/kg from day 7 to day 14 after the induction of myositis was performed was set as a positive control group (FIG. 10).

Example 5.2. Confirmation of Muscle Fibers into Which Inflammation was Infiltrated The mice of each group of Example 5.1 were sacrificed on day 14, and the tissues of the quadriceps and hamstring muscle were collected and stained with H&E, and then the Infiltration of inflammatory cells was observed with an optical microscope. As a result, it was confirmed that the number of the inflammatory cells infiltrated into the muscle fibers in the positive control group and the experimental group was reduced as compared to the negative control group (FIGS. 11 and 12).

In addition, the mice of each group were sacrificed on day 14, and the tissues of the quadriceps and hamstring muscle were collected and stained with H&E, and then the number of muscle fibers into which inflammatory cells were infiltrated was evaluated using a scoring system. The score measurement method of the scoring system was performed the same as in Example 4.2. In this case, the average values of the right and left muscles of the quadriceps and hamstring muscle were compared. As a result, the score of the muscle fibers into which inflammation was infiltrated in the positive control group and the experimental group was significantly reduced as compared to the negative control group (FIG. 13).

Example 5.3. Confirmation of Concentration of Cytokine in Blood

In order to confirm the concentration of IL-1β, IL-6, and TNF-α in the blood of normal mice and mice of each group of Example 5.1 on day 14, serum was isolated from the blood of mice of each group, and then the concentration of IL-1β, IL-6, and TNF-α in the blood was measured using IL-1β ELISA Kit (R&D Systems, Minn., USA), IL-6 ELISA Kit, and TNF-α ELISA Kit (R&D Systems, Minn., USA) according to the manufacturer's manual, respectively.

As a result, it was confirmed that the concentration of IL-6 in the blood was increased in the positive control group as compared to the negative control group, whereas the concentration of IL-6, IL-1β, and TNF-α in the blood was reduced in the experimental group as compared to the negative control group (FIGS. 14, 15, and 16).

Example 5.4. Confirmation of Change in Expression of mRNA of IL-6

The expression level of mRNA of IL-6 was confirmed in mRNA isolated from the muscle of normal mice and mice of each group of Example 5.1 on day 14 through RT-qPCR. Specifically, total RNA was isolated from the muscle using a TRIzol reagent (Invitrogen), and qPCR was performed using SYBR Green (Perkin Elmer, MA, USA) and 7,500 Fast Real-Time PCR system (Applied Biosystems). The experimental results were normalized to the amount of β-actin mRNA. In this case, the primers used are shown in Table 3 below.

TABLE 3

| Primer | Sequence Information | SEQ ID NO. |
|--------|---------------------|------------|
| IL-6-F | TAGTCCTTCCTACCCCAATTTCC | 1 |
| IL-6-R | TTGGTCCTTAGCCACTCCTTC | 2 |

As a result, it was confirmed that the expression of mRNA of IL-6 was reduced in the experimental group. On the other hand, it was confirmed that the expression of mRNA of IL-6 was not reduced in the positive control group, and the experimental group was more effective than the positive control group with respect to the effect of reducing the expression of mRNA of IL-6 (FIG. 17).

Example 5.5. Confirmation of Change in Mitochondrial Function Through Metabolome Analysis After inducing a myositis animal model (CIM), the mitochondrial function was measured in the quadriceps and soleus muscle of a control group, a negative control group (CIM), a positive control group (DEXA), and a group transplanted with 5 μg of mitochondria in cation and anion modes of a CE-TOFMS based metabolome analysis. The samples were diluted as shown in FIG. 37 for measurement by enhancing the analytical quality of the CE-MS analysis.

As can be seen from the analysis of profile heat map of muscle, it was shown that it had a significant influence on the metabolite profile of skeletal muscle of the negative control group (CIM) compared to the control group (FIG. 23). It was confirmed that the metabolite profile of the mitochondria transplantation group was recovered similarly to the metabolite profile of the control group compared to the positive control group (DEXA). The malate-aspartate shuttle (sometimes briefly malate shuttle, malate aspartate shuttle defect) is a biochemical system that translocates electrons produced during the glycolysis process across the semi-permeable inner membrane of the mitochondria for oxidative phosphorylation in eukaryotes.

The mitochondrial dysfunction seen in the myositis model was associated with the malate-aspartate shuttle, and it was confirmed through a decrease in the ratio of relative quantification value of malic acid and aspartate. The ratio of relative quantification value of malic acid and aspartate was significantly increased after the transplantation of mitochondria compared to the negative control group (CIM) and the positive control group (DEXA), and it was confirmed that it was recovered to a level similar to that of the control group (FIGS. 24 to 27).

In conclusion, the therapeutic efficacy of the transplantation of 5μg of mitochondria was confirmed in the CIM mouse model.

Example 6. Confirmation of Effect on Treatment of Myositis According to Administration of Exogenous Mitochondria in Myositis-Induced Mouse Model: Tertiary Experiment

Example 6.1. Experiment Method (n=5)

CFA (Complete Freund's adjuvant) containing 200 μg of C protein fragments and 100 μg of heat-killed Mycobacterium butyricum was intradermally injected into C57BL/6 female 8-week-old mice, and 2 μg of PT (pertussis toxin) was intraperitoneally injected.

A group in which intravenous single administration of the mitochondria isolated in Preparation Example 1 at a dose of 0.2 μg, 1 μg, or 5 μg on day 7 after the induction of myositis was performed was set as an experimental group. In addition, a group in which intraperitoneal administration of 100 μL of PBS was performed was set as a negative control group, and a group in which intraperitoneal administration of dexamethasone (DEXA) at a daily dose of 0.8 mg/kg from day 7 to day 14 after the induction of myositis was performed was set as a positive control group (FIG. 18). As an inflammation evaluation method, myositis after H&E stain was evaluated by dividing the score from 1 to 6 according to histologic severity.

The expression level of inflammatory cytokine in mRNA isolated from the muscle was observed through RT-qPCR. After the transplantation of mitochondria, the level of the activity of mitochondria was evaluated through Western blot analysis of the expression of mitochondria oxidative phosphorylation complex (OXPHOS complexes). The information of animal test group is shown in Table 4 below.

TABLE 4

| Group | Number of Subjects (n) | CIM Induction | Purpose |
|-------|------------------------|---------------|---------|
| Control (non-treat) | 5 | x | control group |
| Vehicle (CIM) | 5 | o | negative control group |
| Dexamethasone | 5 | o | positive control group |
| MT 0.2 ug | 5 | o | experimental group |
| MT 1 ug | 5 | o | experimental group |
| MT 5 ug | 5 | o | experimental group |
| Total number of subjects | 30 | | |

Example 6.2. Confirmation of Inflammation-Infiltrated Muscle Fibers

The mice of each group (Table 4) were sacrificed on day 14, and the tissues of the quadriceps and hamstring muscle were collected and stained with H&E (hematoxylin & eosin), and then the infiltration of inflammatory cells was observed with an optical microscope. As a result, it was confirmed that the number of the inflammatory cells infiltrated into the muscle fibers in the positive control group and the experimental group was reduced as compared to the negative control group (FIG. 19). In addition, the mice of each group were sacrificed on day 14, and the tissues of the quadriceps and hamstring muscle were collected and stained with H&E, and then the number of muscle fibers into which inflammatory cells were infiltrated was evaluated using a scoring system. The score measurement method of the scoring system is shown in Table 5 below. In this case, the average values of the right and left muscles of the quadriceps and hamstring muscle were compared.

TABLE 5

| Score | Evaluation Method (Number of Inflammation-Infiltrated Muscle Fibers) |
|---|---|
| 1 | 1 muscle fiber into which inflammation was infiltrated was observed |
| 2 | 2 to 5 muscle fibers into which inflammation was infiltrated were observed |
| 3 | 6 to 15 muscle fibers into which inflammation was infiltrated were observed |
| 4 | 16 to 30 muscle fibers into which inflammation was infiltrated were observed |
| 5 | 30 to 99 muscle fibers into which inflammation was infiltrated were observed |
| 6 | 100 or more muscle fibers into which inflammation was infiltrated were observed |

As a result, it was confirmed that the number of the inflammatory cells infiltrated into the muscle fibers was significantly reduced in the positive control group and a group in which 5 μg of mitochondria was transplanted compared to the negative control group (FIG. 20).

Example 6.3. Confirmation of Change in
Expression of mRNA of IL-6 and TNF-α

The expression level of mRNA of IL-6 and TNF-α, inflammatory cytokines, was confirmed in mRNA isolated from the muscle of mice of each group in the control group, the negative control group (CIM), the positive control group (DEXA), the experimental group (mitochondria transplantation group) through RT-qPCR. Specifically, total RNA was isolated from the muscle using a TRIzol reagent (Invitrogen), and qPCR was performed using SYBR Green (Perkin Elmer, MA, USA) and 7,500 Fast Real-Time PCR system (Applied Biosystems). The experimental results were normalized to the amount of β-actin mRNA. In this case, the primers used in RT-qPCR are shown in Table 6 below.

TABLE 6

| Primer | Sequence Information | SEQ ID NO. |
|---|---|---|
| IL-6-F | TAGTCCTTCCTACCCCAATTTCC | 1 |
| IL-6-R | TTGGTCCTTAGCCACTCCTTC | 2 |
| TNF-α-F | CCCTCACACTCAGATCATCTTCT | 3 |
| TNF-α-R | GCTACGACGTGGGCTACAG | 4 |

As a result, it was confirmed that the tendency for the expression of mRNA of IL-6 to decrease in the muscles of the mitochondria transplantation group. In addition, it was confirmed that the expression of mRNA of TNF-α was significantly reduced in a group in which 5 μg of mitochondria was transplanted. On the other hand, it was confirmed that the expression of mRNA of IL-6 and TNF-α was not reduced in the muscles of the positive control group (Dexa), and the mitochondria transplantation group was more effective than the positive control group (Dexa) with respect to the effect of reducing the expression of mRNA of IL-6 and TNF-α (FIG. 21).

Example 6.4. Confirmation of Change in
Expression of Oxidative Phosphorylation Complex
of Mitochondria The change in the expression of oxidative phosphorylation complex in proteins isolated from the muscles of mice of each group in the control group, the negative control group (CIM), the positive control group (DEXA), the experimental group (mitochondria transplantation group) was confirmed through western blotting (Total OXPHOS mouse WB Antibody Cocktail, abcam). It was confirmed that the expression of oxidative phosphorylation complex I and II was reduced in the negative control group (CIM) compared to the control group, and the expression of oxidative phosphorylation complex I and II was increased in the experimental group (mitochondria transplantation group) at all doses compared to the positive control group (DEXA) (FIG. 22).

In conclusion, the therapeutic efficacy and dose dependency of the transplantation of 5 μg of mitochondria were confirmed in the CIM mouse model.

IV. Confirmation of Toxicity and Physical
Properties of Composition Comprising
Mitochondria Example 7. Toxicity Experiment In order to confirm that toxicity was shown upon administration of mitochondria, the mitochondria prepared in Preparation Example 1 was administered intravenously once to ICR mice, and then changes in body weight and changes in organs through autopsy and the like were confirmed. 12 male and female 7-week-old ICR mice were divided into four groups as shown in Table 7 below to conduct the experiment.

TABLE 7

| Group | Gender | No. of Subject | Administered Material | Route of Administration | Dosage (μg/subject) | Dosage (mL/subject) | Concentration (μg/mL) |
|---|---|---|---|---|---|---|---|
| G1 | M/F | 3/3 | excipient | IV | — | 0.3 | — |
| G2 | M/F | 3/3 | mitochondria | IV | 25 | 0.3 | 100 |
| G3 | M/F | 3/3 | mitochondria | IV | 50 | 0.3 | 200 |
| G4 | M/F | 3/3 | mitochondria | IV | 100 | 0.3 | 400 |

As shown in Table 7 above, the G1 group was administered with excipients. The G2 to G4 groups were administered with 25 μg, 50 μg, or 100 μg of mitochondria, respectively. At this time, for the G4 group, the mitochondria were administered in an amount of more than an approximate lethal dose (ALD). At this time, the administration site was disinfected with 70% alcohol cotton, and then excipients or mitochondria were administered at a speed of 1 mL/min through the caudal vein using a syringe equipped with a 26 gauge injection needle.

First, the general symptoms were observed for all mice once or more per day, and the type and degree of general symptoms including death during the breeding period were recorded for each subject. However, on the day of administration, observation was continued up to 1 hour after administration, and thereafter observation was performed for 5 hours at an interval of 1 hour. Moribund animals and dead animals were treated in accordance with the planned autopsy animals. The start date of administration of excipients or mitochondria was set as day 1.

As a result of observing general symptoms, no dead animals were observed in all groups during the entire test period, and the abnormal symptoms observed on day 1 after administration of mitochondria were not observed during the subsequent test period, and thus it is considered to be temporary changes caused by the mitochondria. In addition, body weights were measured for all mice subjects before administration, day 2, day 4, day 8, and day 15 after administration. The measurement results are shown in Table 8 below.

Example 8. Comparison of Properties of Mitochondria Isolated from Freeze-Preserved Stem Cells Derived from Umbilical Cord and Mitochondria Isolated from Cultured Stem Cells Derived from Umbilical Cord Mesenchymal stem cells derived from umbilical cord were inoculated into an Alpha-MEM medium containing 10% (v/v) fetal bovine serum (FBS), 100 μg/mL streptomycin, and 100 U/mL ampicillin and cultured for 72 hours. The cultured cells were treated with 0.25% Trypsin-EDTA (TE) to obtain the cells. The obtained cells were resuspended in a concentration of $1 \times 10^7$ cells/mL using a hemocytometer, then placed in a freezing tube, transferred to a cryopreservation container, then frozen at a temperature of –80° C. for 24 hours, and stored in a liquid nitrogen cryopreservation bank. The mitochondria isolated from freeze-preserved stem cells derived from umbilical cord were isolated in the same manner as in Preparation Example 1 above, and compared to the cultured cells-derived mitochondria isolated in Preparation Example 1 in terms of the properties of ATP activity, membrane potential, and mitochondrial reactive oxygen species.

As a result, in order to compare the ability of ATP synthesis between mitochondria isolated from freeze-preserved stem cells derived from umbilical cord and mitochondria isolated from cultured stem cells derived from umbilical cord, it was confirmed that a substrate (ADDP) was added and the ATP activity was recovered to a similar ratio in both conditions compared to basal energy metabolism. In addition, it was confirmed that the membrane potential activity was similar in both conditions, and the

TABLE 8

| | Body Weight of Male Mouse (g) Group | | | | Body Weight of Female Mouse (g) Group | | | |
|---|---|---|---|---|---|---|---|---|
| Day | G1 | G2 | G3 | G4 | G1 | G2 | G3 | G4 |
| 1 | 37.48 ± 1.78 | 37.88 ± 1.11 | 37.94 ± 1.18 | 38.02 ± 1.07 | 29.12 ± 1.36 | 29.09 ± 1.28 | 29.18 ± 0.99 | 29.32 ± 0.93 |
| 2 | 37.62 ± 1.55 | 38.06 ± 0.55 | 36.46 ± 1.71 | 36.59 ± 1.45 | 29.23 ± 1.48 | 28.96 ± 0.76 | 28.93 ± 0.76 | 28.21 ± 0.96 |
| 4 | 37.50 ± 1.86 | 37.88 ± 0.66 | 36.61 ± 2.17 | 37.46 ± 1.55 | 28.99 ± 0.96 | 28.97 ± .61 | 29.54 ± 1.62 | 28.51 ± 1.09 |
| 8 | 38.49 ± 1.53 | 38.75 ± 1.65 | 37.12 ± 3.09 | 38.96 ± 1.79 | 29.13 ± 0.71 | 29.58 ± 0.27 | 29.90 ± 1.78 | 28.92 ± 1.79 |
| 15 | 39.21 ± 1.11 | 39.19 ± 1.17 | 37.73 ± 2.85 | 39.98 ± 1.39 | 30.56 ± 0.52 | 30.22 ± 0.45 | 30.82 ± 1.43 | 29.70 ± 1.39 |
| N | 3 | 3 | 3 | 3 | 3 | 3 | 3 | 3 |

As shown in Table 8, no significant change in body weight was observed in the G1 to G4 groups. In addition, all of the mice subjects were anesthetized on day 15, and then cut the abdomen open and visually examined for all organs. As a result, no change in organs was observed in the G1 to G4 groups.

Based on the above results, it was confirmed that when intravenous single administration of the mitochondria to the ICR mice under these test conditions was performed, both male and female showed no toxicity in a concentration of mitochondria up to 100 μg/head.

production of mitochondrial reactive oxygen species was also similar (FIGS. 28 to 30).

Example 9. Measurement of Number of Mitochondria Using Particle Counter

Each solution of mitochondria isolated from mesenchymal stem cells derived from human umbilical cord isolated in Preparation Example 1 was prepared at a concentration of 1 μg/mL, 2.5 μg/mL, and 5 μg/mL, and then the number of the mitochondria was measured through a particle counter (Multisizer 4e, Beckman Coulter). At this time, it was measured twice for each concentration, and the measurement results are shown in Table 9 below and FIGS. 31 to 33.

TABLE 9

| No. of | 1 μg/mℓ | | 2.5 μg/mℓ | | 5 μg/mℓ | |
|---|---|---|---|---|---|---|
| | 1st | 2nd | 1st | 2nd | 1st | 2nd |
| mitochondria/mℓ | 2.66E±06 | 1.25E±06 | 6.11E±06 | 5.83E±06 | 1.24E±07 | 7.83E±06 |
| average | $1.96 \times 10^6 \pm 0.98 \times 10^6$ | | $5.97 \times 10^6 \pm 0.19 \times 10^6$ | | $1.01 \times 10^7 \pm 0.32 \times 10^7$ | |

V. Confirmation of Anti-Inflammatory Effect by Mitochondria In Vitro

Example 10. Comparison of Anti-Inflammatory Activity Using Quantitative Real-Time Polymerase Chain Reaction by Mitochondria Derived from Several Kinds of Cells in Raw264.7 Cells In order to compare and analyze the anti-inflammatory activity by mitochondria obtained from various cells by the methods of Example 2, Example 3, Example 4, and Example 7, cells based analysis experiment using a quantitative real-time polymerase chain reaction was conducted.

RAW264.7 cells, a macrophage cell line derived from mice, were cultured in a DMEM medium containing 10% FBS. About $3 \times 10^5$ cells/well were inoculated into a 6 well plate, and cultured for 24 hours, and then deficiency condition in a DMEM medium from which FBS was removed was maintained for about 24 hours.

After 24 hours, it was treated with salmonella-derived lipopolysaccharide (LPS) in a concentration of 1 μg/mL for 6 hours to induce an inflammatory response in a macrophage cell line. After 6 hours of lipopolysaccharide treatment, the cells were washed twice with PBS buffer solution, and then treated with the mitochondria obtained from each cell and further cultured for 18 hours. In this case, the negative control group is a group that is not treated with lipopolysaccharide and mitochondria, and the positive control group is a group that is treated with lipopolysaccharide in a concentration of 1 μg/mL alone. In addition, the experimental group was treated with lipopolysaccharide in a concentration of 1 μg/mL, and after 6 hours, treated with the mitochondria obtained from mesenchymal stem cells derived from bone marrow (BM-MSC), mesenchymal stem cells derived from umbilical cord (UC-MSC), rat myoblasts (L6 myoblast), and fibroblasts derived from human lung (CCD-8LU) at an amount of 30 μg, respectively.

After 18 hours of mitochondrial treatment, the culture solution was removed, and the cells were washed twice by adding PBS buffer solution to the cells, 0.5 mL of RNA extract (Trizol reagent, Thermo Fisher Scientific) was added directly, and then left at ambient temperature for 10 minutes. Then, 0.1 mL of chloroform was added and stirred for 15 seconds, and then centrifuged at about 12,000×g for 10 minutes.

The separated supernatant was obtained, and the same volume of isopropyl alcohol was added, and then centrifuged at 12,000×g for 10 minutes. Thereafter, the liquid was removed and washed once with 75% ethanol, and then dried at ambient temperature. After drying, about 50 μL of RNAase-free purified distilled water was added, and the quantity and purity of the obtained RNA was measured using a spectrophotometer.

In order to synthesize cDNA using the obtained RNA, 2 μg of purified total RNA was subjected to a binding reaction with oligo dT for 5 minutes at 70° C., and then 10× reverse transcription buffer solution, 10 mM dNTP, RNAse inhibitor, and M-MLV reverse transcriptase (Enzynomics, Korea) were added, and cDNA synthesis reaction was performed at 42° C. for 60 minutes.

After the cDNA synthesis reaction was completed, the reverse transcriptase was inactivated by heating at 72° C. for 5 minutes, and then RNase H was added to remove single-stranded RNA to obtain a final cDNA. The changes in the expression of TNF-α gene, IL-1β gene, and IL-6 gene, which are characteristic genes of inflammatory response, were observed through a quantitative real-time polymerase chain reaction. GAPDH gene was quantified along with them to correct the difference in expression. The base sequences of the genes used in the quantitative real-time polymerase chain reaction are as described in Table 10 below.

TABLE 10

| Primer | Sequence |
|---|---|
| TNF-alpha-S | 5'-TCTCATCAGTTCTATGGCCC-3' (SEQ ID NO: 5) |
| TNF-alpha-AS | 5'-GGGAGTAGACAAGGTACAAC-3' (SEQ ID NO: 6) |
| IL-1beta-F | 5'-AACCTGCTGGTGTGTGACGTTC-3' (SEQ ID NO: 7) |
| IL-1beta-R | 5'-CAGCACGAGGCTTTTTTGTTGT-3' (SEQ ID NO: 8) |
| IL-6-AS | 5'-CTAGGTTTGCCGAGTAGATCT-3' (SEQ ID NO: 9) |
| IL-6-S | 5'-CCAAACTGGATATAATCAGGAAAT-3' (SEQ ID NO: 10) |
| GAPDH-S | 5'-GGTGAAGGTCGGTGTGAAG-3' (SEQ ID NO: 11) |
| GAPDH-AS | 5'-CTCGCTCCTGGAAGATGGTG-3' (SEQ ID NO: 12) |

As shown in the experimental results, it was found that the expression of TNF-α, IL-1β, and IL-6 genes was increased when RAW 264.7 cells, a mouse macrophage cell line, were treated with lipopolysaccharide. In addition, it was confirmed that the expression of TNF-α, IL-1β, and IL-6 genes induced by lipopolysaccharide was inhibited to a significant level when treated with the mitochondria obtained from mesenchymal stem cells derived from bone marrow, mesenchymal stem cells derived from umbilical cord, rat myoblasts, and fibroblasts derived from human lung. Based on the above, it was confirmed that the mitochondria obtained from the cells used in the present invention exhibited a remarkably excellent anti-inflammatory activity (FIG. 34).

Example 11. Comparison of Anti-Inflammatory Activity by Mitochondria Derived from Several Kinds of Cells in Human Mononuclear Cells (THP-1)

THP-1 cells, human-derived mononuclear cells, were cultured in an RPMI medium containing 10% FBS. $4 \times 10^5$ cells/well were inoculated into a 24 well plate, and cultured for 15 to 16 hours in a RPMI medium containing 1% FBS.

The cells were treated with salmonella-derived lipopolysaccharide (LPS) in a concentration of 2 µg/mL for 6 hours to induce an inflammatory response in a THP-1 cell line. After 6 hours of lipopolysaccharide treatment, the cells were treated with the mitochondria obtained from each cell and further cultured for 24 hours. In this case, the negative control group is a group that is not treated with lipopolysaccharide and mitochondria, and the positive control group is a group that is treated with lipopolysaccharide in a concentration of 2 µg/mL alone. In addition, the experimental group was treated with lipopolysaccharide in a concentration of 2 µg/mL, and after 6 hours, treated with the mitochondria obtained from mesenchymal stem cells derived from umbilical cord (UC-MSC), fibroblasts derived from human lung (CCD-8LU), human induced pluripotent stem cells (IPS), and porcine platelets obtained by the methods of Example 2, Example 4, Example 5, and Example 6 at an amount of 40 µg, respectively. In order to compare the anti-inflammatory activity after the reaction, the cells were used for a quantitative real-time polymerase chain reaction, and the culture solution was used for ELISA.

Example 11.1. Comparison of Anti-Inflammatory Activity Using Quantitative Real-Time Polymerase Chain Reaction Thereafter, the culture solution was removed, and PBS buffer solution was added to the cells, washed twice, and 0.5 mL of RNA extract (Trizol reagent, Thermo Fisher Scientific) was added directly. After standing at ambient temperature for 10 minutes, 0.1 mL of chloroform was added and stirred for 15 seconds, and then centrifuged at 12,000×g for 10 minutes. The separated supernatant was taken, and the same volume of isopropyl alcohol was added, centrifuged at 12,000×g for 10 minutes, and then the supernatant was removed, washed once with 75% ethanol, and dried at ambient temperature.

50 µL of RNAase-free purified distilled water was added, and the quantity and purity of the obtained RNA was measured using a spectrophotometer. In order to synthesize cDNA, 2 µg of purified total RNA was subjected to a binding reaction with oligo dT for 5 minutes at 70° C., and then 10× reverse transcription buffer solution, 10 mM dNTP, RNAse inhibitor, and M-MLV reverse transcriptase (Enzynomics, Korea) were added, and cDNA synthesis reaction was performed at 42° C. for 60 minutes. After the reaction, the reverse transcriptase was inactivated by heating at 72° C. for 5 minutes, and then RNase H was added to remove single-stranded RNA to obtain cDNA.

Quantitative polymerase chain reaction (quantitative RT-PCR) was performed using primers shown in Table 11 below to determine whether expression of pro-inflammatory cytokines was changed. In this case, the difference in expression was corrected by quantifying with 18S as a gene for correction.

TABLE 11

| Primer | Base Sequence |
| --- | --- |
| Human IL-6-S | ccacacagacagccactcac (SEQ ID NO: 13) |
| Human IL-6-AS | tttcaccaggcaagtctcct (SEQ ID NO: 14) |

TABLE 11-continued

| Primer | Base Sequence |
| --- | --- |
| Human 18S-S | ctcccacttggataactgtgg (SEQ ID NO: 15) |
| Human 18S-AS | gaccgggttggttttgatct (SEQ ID NO: 16) |

As shown in the experimental results, it was found that the expression of IL-6 gene was increased when THP-1 cells, which are human mononuclear cells, were treated with lipopolysaccharide. In addition, it was confirmed that the expression of IL-6 gene induced by lipopolysaccharide was inhibited to a significant level when treated with the mitochondria obtained from mesenchymal stem cells derived from umbilical cord, fibroblasts derived from human lung, human induced pluripotent stem cells, and porcine platelets. Based on the above, it was confirmed that the mitochondria obtained from various cells exhibited a remarkably excellent anti-inflammatory activity (FIG. 35, *P<0.05).

Example 11.2. Comparison of Anti-Inflammatory Activity Using Elisa Method

In order to confirm the expression level of IL-6, a pro-inflammatory cytokine of THP-1 cells with the obtained supernatant, the experiment was conducted using Human IL-6 (R&D Systems) according to the manufacturer's manual as follows.

100 µL of coating solution was put into a 96-well plate, reacted overnight at ambient temperature, washed 3 times, then reacted with reagent diluent for 1 hour at ambient temperature, and washed 3 times. The 10-fold diluted supernatant and the standard solution were reacted for 2 hours at ambient temperature, then washed 3 times, and then treated with the labeled antibody (detection antibody) in each well, and then reacted for 2 hours at ambient temperature. After washing 3 times, the streptavidine solution (streptavidine-HRP) was reacted for 20 minutes at ambient temperature, then washed 3 times, then reacted with the color solution (substrate solution) in a dark room at ambient temperature for 20 minutes, and then the reaction stop solution was added, and the absorbance was measured at a wavelength of 450 nm.

As shown in the experimental results, it was found that IL-6 protein was increased when THP-1 cells, which are human mononuclear cells, were treated with lipopolysaccharide. In addition, it was confirmed that the IL-6 protein induced by lipopolysaccharide was inhibited to a significant level when treated with the mitochondria obtained from mesenchymal stem cells derived from umbilical cord, fibroblasts derived from human lung, human induced pluripotent stem cells, and porcine platelets, and it was consistent with the results of gene expression. Based on the above, it was confirmed that the mitochondria obtained from various cells exhibited a remarkably excellent anti-inflammatory activity (FIG. 36, *P<0.05).

The invention claimed is:

1. A method for treating myositis, comprising a step of administering to a subject in need thereof a pharmaceutical composition comprising isolated mitochondria as an active ingredient, wherein the myositis is polymyositis or dermatomyositis, wherein the isolated mitochondria are isolated from mesenchymal stem cells.

2. The method of claim 1, wherein the isolated mitochondria are isolated from cells cultured in vitro.

3. The method of claim 1, wherein the mesenchymal stem cell is obtained from any one selected from the group consisting of umbilical cord, umbilical cord blood, bone marrow, fat, muscle, nerve, skin, amniotic membrane, placenta, synovial fluid, testis, periosteum, and a combination thereof.

4. The method of claim 1, wherein the isolated mitochondria are comprised in a concentration of 0.1 μg/mL to 1000 μg/mL with respect to the pharmaceutical composition.

5. The method of claim 1, wherein the isolated mitochondria are comprised at a content of $1 \times 10^5$ to $5 \times 10^8$ mitochondria/mL with respect to the pharmaceutical composition.

6. The method of claim 1, wherein the pharmaceutical composition is administrated intravenously, intramuscularly, or intradermally.

* * * * *